US008628971B2

(12) United States Patent
Fritchie et al.

(10) Patent No.: US 8,628,971 B2
(45) Date of Patent: Jan. 14, 2014

(54) SYSTEMS AND METHODS FOR MANAGING INVENTORIES OF REAGENTS

(71) Applicants: Patrick P. Fritchie, SouthLake, TX (US); John C. Jones, Grapevine, TX (US); Oscar F. Schwartz, Arlington, TX (US)

(72) Inventors: Patrick P. Fritchie, SouthLake, TX (US); John C. Jones, Grapevine, TX (US); Oscar F. Schwartz, Arlington, TX (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/664,113

(22) Filed: Oct. 30, 2012

(65) Prior Publication Data

US 2013/0137093 A1 May 30, 2013

Related U.S. Application Data

(63) Continuation of application No. 12/486,481, filed on Jun. 17, 2009, now Pat. No. 8,318,499.

(51) Int. Cl.
*G01N 35/00* (2006.01)

(52) U.S. Cl.
USPC .......................................................... 436/43

(58) Field of Classification Search
USPC .................................. 436/43; 435/6.1, 287.2
See application file for complete search history.

(56) References Cited

U.S. PATENT DOCUMENTS

| | | | |
|---|---|---|---|
| 5,417,922 A | 5/1995 | Markin et al. | |
| 5,427,743 A | 6/1995 | Markin | |
| 5,589,137 A | 12/1996 | Markin et al. | |
| 5,795,784 A | 8/1998 | Arnquist et al. | |
| 5,856,194 A | 1/1999 | Arnquist et al. | |
| 6,074,615 A | 6/2000 | Lewis et al. | |
| 6,343,690 B1 | 2/2002 | Britton et al. | |
| 6,555,062 B1 | 4/2003 | Lewis et al. | |
| 6,919,795 B2 | 7/2005 | Roseen | |
| 6,983,884 B2 | 1/2006 | Auchinleck | |
| 8,035,485 B2 | 10/2011 | Fritchie | |
| 2007/0172396 A1 | 7/2007 | Neeper et al. | |
| 2008/0024301 A1* | 1/2008 | Fritchie et al. | 340/572.1 |
| 2009/0003981 A1 | 1/2009 | Miller | |
| 2009/0117620 A1 | 5/2009 | Fritchie et al. | |
| 2009/0181359 A1 | 7/2009 | Lou et al. | |
| 2010/0123551 A1 | 5/2010 | Fritchie | |

FOREIGN PATENT DOCUMENTS

| | | |
|---|---|---|
| EP | 1757882 | 2/2001 |
| EP | 1391401 | 2/2004 |
| JP | 2007315784 A | 12/2007 |
| JP | 2007333466 | 12/2007 |

OTHER PUBLICATIONS

International Preliminary Report on Patentability, issued by the International Bureau of WIPO in connection with application No. PCT/US2010/038519, on Dec. 20, 2011, 6 pages.
International Search Report, issued by the International Searching Authority in connection with application No. PCT/US2010/038519, on Nov. 24, 2010, 3 pages.
Architect System Operations Manual (PN 201837-106), Jan. 2009, sections 1-143-1-148, 6 pages.
Stewart, "Introduction to Real Time," Embedded Systems Design, Embededded.com, Nov. 1, 2001, 4 pages.
Office action, issued by the United States Patent and Trademark Office in connection with U.S. Appl. No. 12/486,481, on Nov. 23, 2010, 15 pages.
Final rejection, issued by the United States Patent and Trademark Office in connection with U.S. Appl. No. 12/486,481, on May 13, 2011, 20 pages.
Office action, issued by the United States Patent and Trademark Office in connection with U.S. Appl. No. 12/486,481, on Sep. 29, 2011, 20 pages.
Final rejection, issued by the United States Patent and Trademark Office in connection with U.S. Appl. No. 12/486,481, on Feb. 24, 2012, 21 pages.
Notice of Allowance and Fee(s) Due, issued by the United States Patent and Trademark Office in connection with U.S. Appl. No. 12/486,481, on Jul. 16, 2012, 10 pages.
Advisory Action, issued by the United States Patent and Trademark Office in connection with U.S. Appl. No. 12/486,481, on Jun. 8, 2012, 3 pages.

* cited by examiner

*Primary Examiner* — Christine T Mui
(74) *Attorney, Agent, or Firm* — Hanley Flight & Zimmerman, LLC

(57) ABSTRACT

A system for managing the inventory of reagents for a laboratory automation system. The system for managing the inventory of reagents comprises a controller, software for the controller, and a refrigerator capable of refrigerating reagents, detecting the presence or absence of reagents in the refrigerator, and detecting the location of reagents in the refrigerator. The system for managing the inventory of reagents is connected to a laboratory automation system. The laboratory automation system comprises at least one clinical analyzer. A typical system for managing inventories of reagents includes an operator interface for the loading of boxes of reagents and other supplies, radio frequency identification system for identification of inventory and tracking, robotic mechanisms for loading containers onto the track system and removing containers from the track system, decapping equipment, refrigeration equipment, and information technology connections to laboratory analyzers and vendors.

14 Claims, 17 Drawing Sheets

SYSTEMS AND METHODS FOR MANAGING INVENTORIES OF REAGENTS

RELATED APPLICATION

This patent is a continuation of U.S. patent application Ser. No. 12/486,481 (now U.S. Pat. No. 8,318,499), filed Jun. 17, 2009, entitled "System for Managing Inventories of Reagents," which is hereby incorporated herein in its entirety.

FIELD OF THE DISCLOSURE

This disclosure relates generally to management of inventories, more particularly, management of inventories of reagents for a laboratory automation system.

BACKGROUND

Automated analyzers are well-known in the field of clinical chemistry and in the field of immunochemistry. Representative examples of such automated analyzers include, but are not limited to, PRISM® analyzers, AxSym® analyzers, ARCHITECT® analyzers, all of which are commercially available from Abbott Laboratories, Cobas® 6000, commercially available from Roche Diagnostics, Advia, commercially available from Siemens AG, Dimension Vista, commercially available from Dade Behring Inc., Unicel® DxC600i, commercially available from Beckman Coulter Inc., and VITROS, commercially available from Ortho-Clinical Diagnostics. Each of these analyzers suffers from various shortcomings, some more than others. Some of the shortcomings encountered by more than one of these automated analyzers include the use of large volumes of sample, the use of large volumes of reagents, the generation of large volumes of liquid waste and solid waste, and high costs. Some of the aforementioned automated analyzers are not designed so as to be able to carry out both clinical chemistry assays and immunoassays. Some of the aforementioned automated analyzers are not capable of being modified to suit the demands of certain users. For example, even if a user desires to have more immunoassay reagents on an analyzer and fewer clinical chemistry reagents on the analyzer, or vice versa, the user cannot modify the configuration. Furthermore, the addition of additional immunoassay modules and/or clinical chemistry modules to increase throughput is difficult, if not impossible. Some of the aforementioned automated analyzers require a great deal of maintenance, both scheduled and unscheduled. In addition, some of the aforementioned automated analyzers have scheduling protocols for assays that cannot be varied, i.e., the assay scheduling protocols are fixed, which limits such features as throughput. For example, modification of current assay protocols or addition of new assay protocols may be difficult, if not impossible. The ARCHITECT® analyzers currently in use can only support six variants of chemiluminenscent microparticle immunoassay protocols. In addition, some of the aforementioned analyzers occupy a great deal of floor space and consume large quantities of energy.

Users of automated analyzers desire the automated analyzers to have a minimal effect on laboratory operations, e.g., reduction of quantities of reagents and samples used, simplification of ordering of consumable items. Users of automated analyzers further desire more automation of processes, e.g., automated loading of reagents, automated loading of other consumable items. Users of automated analyzers still further desire safer and more reliable apparatus, e.g., minimal quantity of unexpected failures, minimal down-time, minimal time required to diagnose and repair unexpected failures. Users of automated apparatus further desire quiet apparatus and environmentally friendly apparatus.

Currently, the management of reagents and other consumable items used in automated clinical analyzers is performed manually. Customers load reagents and consumable items onto automated clinical analyzers based on need, i.e., low inventory, calibration status, i.e., calibrated lots are used first, expiration date, i.e., oldest items are used first, and menu distribution, i.e., maximization of laboratory throughput. In addition, customers track the usage of reagents and consumable items and manually order replacement items to maintain a reasonable inventory. In addition, customers manually sort reagents to remove recalled products and to manually distribute literature relating to data on the safety of materials, package inserts, and assay protocols. Still further, customers track temperature of the reagents during shipping and storage. Still further, positive identification of consumable items is essential in many industries, and tracking of lots used to manufacture or test a product is considered good manufacturing practice. It would be desirable to automate as many as possible of the functions normally carried out the manage reagents and other consumable items.

SUMMARY

In one aspect, this disclosure provides a system for managing the inventory of reagents for a laboratory automation system. The system for managing the inventory of reagents comprises a controller, software for the controller, and a refrigerator capable of refrigerating reagents, detecting the presence or absence of reagents in the refrigerator, and detecting the location of reagents in the refrigerator. The system for managing the inventory of reagents is connected to a laboratory automation system. The laboratory automation system comprises at least one clinical analyzer.

A typical system for managing inventories of reagents includes an operator interface for the loading of boxes of reagents and other supplies, radio frequency identification system for identification of inventory and tracking, robotic mechanisms for loading containers onto the track system and removing containers from the track system, de-capping equipment, refrigeration equipment, and information technology connections to laboratory analyzers and vendors.

The system for managing the inventory of reagents described herein includes a method of reading information from labels. According to this method, radio frequency identification tags, conforming to the guidelines of ISO 14443 or ISO 15693 and ISO 18000, are positioned on the items of interest, such as, for example, reagent containers, sample containers, and micro-well plates. These tags can be read by and written to by a stationary antenna of a radio frequency identification reader. Reading of radio frequency identification tags and writing to radio frequency identification tags are controlled by software. The use of radio frequency identification technology provides faster and more reliable readings than do barcodes, and further eliminates the hazards associated with laser scanning devices.

The system for managing the inventory of reagents described herein provides a user-friendly graphical user interface for enabling an operator to closely control and monitor numerous immunoassays and/or clinical chemistry assays. The graphical user interface can utilize fuel gauge-type liquid level indicators to simplify reading of liquid levels in containers. The graphical user interface can utilize instructional balloons to instruct relatively inexperienced operators in proper usage of the laboratory automation system.

In the system for managing the inventory of reagents described herein, storage of reagent containers, transfer of reagent containers, and refrigeration of reagents in reagent containers can be effected with little difficulty. Reagent containers can be transferred from a refrigerated storage area to the analysis section of the laboratory automation system by an automated robotic mechanism.

Manual loading of reagents and samples can be eliminated by using automated systems. In addition, ordering of reagents and other consumable items can be automated by means of a system for managing inventories of reagents, which can communicate with on-line order entry systems available from many vendors. The system for managing the inventory of reagents described herein provides substantial labor savings and quality improvements relative to manual management of inventory of reagents and consumable items.

The system for managing the inventory of reagents described herein can manage inventories of reagents and consumable items with data that can be encoded on a radio frequency identification tag. For example, if a partially used reagent container is moved to a new system, that system can determine how many assays remain in the container, when the container was opened, and temperature tracking data for reagent shipping and storage, by reading the data that is stored on a radio frequency identification tag.

Expiration dates, calibration status, and reagent inventory needs of clinical analyzers can be monitored to provide automated reagent loading and ordering. These features allow laboratories to save labor that is typically allocated to these functions.

BRIEF DESCRIPTION OF THE DRAWINGS

FIG. 2 depicts components that can be positioned adjacent to the track system shown in FIG. 1.

DETAILED DESCRIPTION

Figure 1:
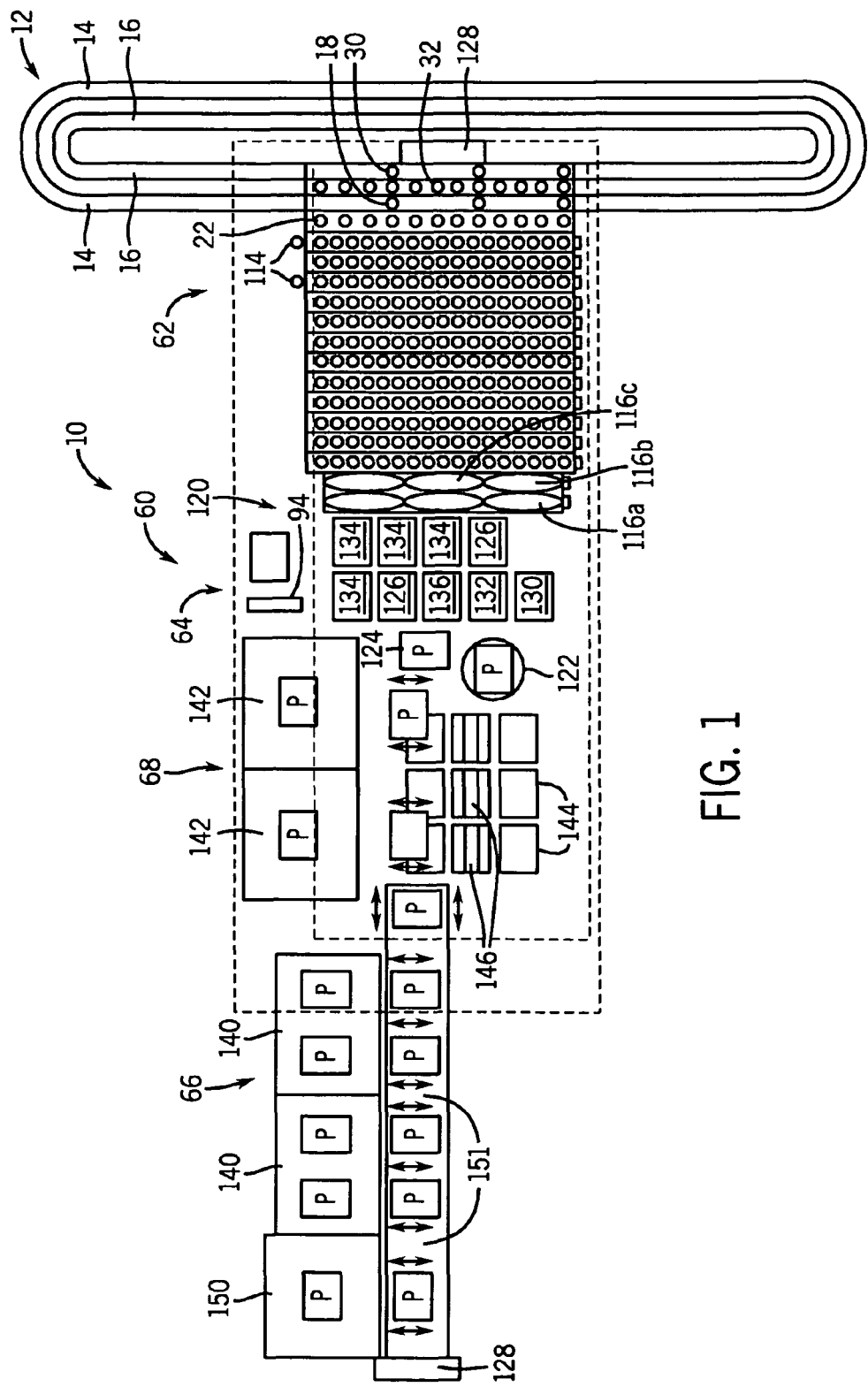
FIG. 1 is a schematic diagram of a laboratory automation system that utilizes reagents from the system for managing the inventory of reagents described herein.

As used herein, the expression "radio frequency identification", or "RFID", is a generic term for technologies that use radio waves to automatically identify objects, such as, for example, containers for biological samples and containers for reagents for analyzing biological samples. The most common method of identification is to store a serial number that identifies the object, and perhaps other information relating to the object or contents thereof, on a microchip that is attached to an antenna. The microchip and the antenna together are called a radio frequency identification transponder or a radio frequency identification tag. The antenna enables the microchip to transmit the identification information and other information to an antenna connected to a radio frequency identification reader. The radio frequency identification reader converts the radio waves transmitted from the radio frequency identification tag into digital information that can then be passed on to computers that can make use of it.

As used herein, the expression "radio frequency identification system", or "RFID system", comprises a radio frequency identification tag made up of a microchip with an antenna, and a radio frequency identification interrogator or radio frequency identification reader with an antenna. The radio frequency identification reader sends out electromagnetic waves. The tag antenna is tuned to receive these waves. A passive radio frequency identification tag draws power from the field created by the reader and uses it to power the circuits of the microchip. The microchip then modulates the waves that the passive radio frequency identification tag sends back to the radio frequency identification reader, which converts the waves received by the radio frequency identification reader into digital data.

As used herein, microchips in radio frequency identification tags can be "read-write microchips", "read-only microchips", or "write once, read many microchips." In the case of read-write microchips, information can be added to the radio frequency identification tag or existing information can be written over when the radio frequency identification tag is within range of a radio frequency identification reader. Read-write microchips usually have a serial number that cannot be written over. Additional blocks of data can be used to store additional information about the items to which the radio frequency identification tag is attached. These radio frequency identification tags can be locked to prevent overwriting of data or encrypted to prevent the disclosure of proprietary data or disclosure of data that would compromise the privacy of a patient. Read-only microchips have information stored on them during the manufacturing process. The information on them can never be changed. Write once, read many microchips have a serial number and other data written to them once, and that information cannot be overwritten later.

Active radio frequency identification tags have a transmitter and their own power source, typically a battery. The power source is used to run the microchip's circuitry and to broadcast a signal to a radio frequency identification reader. The microchip's circuitry can possibly perform some sort of monitoring function. Passive radio frequency identification tags have no battery. Instead, passive radio frequency identification tags draw power from the radio frequency identification reader, which sends out electromagnetic waves that induce a current in the tag's antenna. Semi-passive radio frequency identification tags use a battery to run the microchip's circuitry, but communicate by drawing power from the radio frequency identification reader. Any of the foregoing types of radio frequency identification tags can be used in the system of this disclosure.

As used herein, the expression "radio frequency identification reader" or "reader" means a device having the function of providing means for communicating with a radio frequency identification tag and facilitating transfer of data to and from a radio frequency identification tag. Functions performed by a radio frequency identification reader can include quite sophisticated signal conditioning, signal sorting, parity error checking, and correction. Once the signal from a radio frequency identification tag has been correctly received and decoded, algorithms can be applied to decide whether the signal is a repeat transmission, and can then instruct the radio frequency identification tag to cease transmitting. This type of interrogation is known as "command response protocol" and is used to circumvent the problem of reading a plurality of radio frequency identification tags in a short space of time. An alternative technique involves the radio frequency identification reader looking for radio frequency identification tags with specific identities, and interrogating them in turn. It is within the scope of this disclosure to use a single radio frequency identification reader or a plurality of radio frequency identification readers. A radio frequency identification reader is connected to a single antenna or to a plurality of antennas.

As used herein, the expression "analysis section of the laboratory automation system" means that portion of the laboratory automation system in which immunoassays or clinical chemistry assays or both immunoassays and clinical chemistry assays are performed. As used herein, the expression "aspirating/dispensing device" means a device that has the dual functions of removing liquids from containers by suction and distributing portions of the liquids aspirated into containers, e.g., micro-wells of micro-well plates. An aspirating/dispensing device that is capable of being used for the system described herein is described in U.S. Pat. No. 7,033,543, incorporated herein by reference. As used herein, the term "XYZ" refers to a device that can move in three directions, a first horizontal direction, a second horizontal direction that is perpendicular to the first horizontal direction, and a third direction that is perpendicular to both the first horizontal direction and the second horizontal direction. As used herein, the term "kitting" means dispensing samples and reagents in appropriate micro-wells of a micro-well plate prior to commencing chemical reactions.

As used herein, the expression "pick and place robot", and the like, means a robot that is capable of retrieving an object from a given location and transferring that object to another location.

As used herein the expression "smart refrigerator" means a refrigerator that incorporates radio frequency identification technology for detecting and identifying refrigerated items contained therein. The radio frequency can be high frequency (e.g., 13.56 MHz) or ultra high frequency (e.g., 900 MHz). The smart refrigerator can be provided by the assignee or by other suppliers.

As used herein, the expression "laboratory automation system" means a system designed to automate the processing of samples prior to, during, and subsequent to analyzing the samples. The processing includes handling of the samples, moving the samples from a clinical analyzer to other components of the system, and storing of the samples. As used herein, the expression "clinical analyzer" includes, but is not limited to, immunoassay analyzers, clinical chemistry analyzers, and apparatus for extraction of nucleic acids from a biological sample and amplification of the nucleic acids thus extracted. As used herein, the expressions "controller for the reagent inventory management system", "reagent inventory management controller", and the like, mean the computer hardware and the computer software that interfaces with the smart refrigerator. The controller for the reagent inventory management system can be a personal computer.

As used herein, the expression "antenna board" means an apparatus that comprises one or more devices, typically formed from metal but not limited to being formed from metal, that is (are) capable of sending and receiving radio waves. These devices can be an array of traces printed on a circuit board, or devices formed by wires and separated by insulators. Each antenna can be selected individually, and can read one specific location or one specific area. Additional information relating to antenna boards suitable for use herein are described in U.S. patent application Ser. No. 11/495,430, filed Jul. 28, 2006, and entitled SYSTEM FOR TRACKING VESSELS IN AUTOMATED LABORATORY ANALYZERS BY RADIO FREQUENCY IDENTIFICATION and U.S. patent application Ser. No. 12/274,479, filed Nov. 20, 2008, and entitled SYSTEM FOR TRACKING VESSELS IN AUTOMATED LABORATORY ANALYZERS BY RADIO FREQUENCY IDENTIFICATION, both of which are incorporated herein by reference.

As used herein, the term "immunoassay" means a biochemical test that measures the concentration of a substance in a biological liquid, typically serum, using the reaction of an antibody or antibodies to its (their) antigen. An immunoassay takes advantage of the specific binding of an antibody to its antigen. As used herein, a "chemiluminescent microparticle immunoassay", alternatively referred to as "chemiluminescent magnetic immunoassay", involves a chemiluminescent label conjugated to the antibody or the antigen. In this assay, a magnetic microparticle is coated with antibodies. The assay is intended to look for antigens in the sample. A second antibody is labeled with a chemiluminescent label. This second antibody is not attached to a magnetic microparticle. The antibody and antigen with attach in the following order: antibody on magnetic microparticle-antigen-antibody-chemiluminescent label. The magnetic microparticle is then washed off. The amount of antibody-antigen-enzyme is measured by adding pre-trigger solution and trigger solution and measuring the light produced. This type of immunoassay produces light when combined with its substrate, i.e., a specific binding member. The chemiluminescent reaction offers high sensitivity and ease of measurement. This type of immunoassay involves a noncompetitive sandwich format that yields results that are directly proportional to the amount of analyte present in the sample. As used herein, the term "magnetic" means paramagnetic.

As used herein, the expression "clinical chemistry assay" means a biochemical test that measures the concentration of a substance that occurs naturally within the human body, which concentrations serves to indicate the condition or state of health of the various systems of the body. Such a substance, often referred to as an analyte, exists within certain expected ranges of concentration in a healthy human being. Chemistry analytes fall into one of three main categories, routine analytes, such as for example, lipids, nutrients, chemical constituents, metabolic products, examples of which include glucose, urea nitrogen triglycerides, uric acid, enzymes, such as, for example, alanine aminotransferase, aspartate aminotransferase, lactate dehydrogenase, and amylase, and electrolytes, such as, for example, sodium, potassium, and chloride.

As used herein, the term "calibrator" means a composition containing a known concentration of an analyte for use in determining the concentration of the analyte in a sample containing an unknown concentration of the analyte. As used herein, the term "control" means a composition containing a known concentration of an analyte for use in controlling the quality of results in a clinical analyzer. As used herein, the expression "bulk liquid" means a liquid, typically a reagent, a wash buffer, a diluent, or some other type of treating agent in liquid form, which liquid is provided in a relatively large volume, such as, for example, one liter or greater.

As used herein, the term "system" means a group of interrelated, interacting, or interdependent constituents forming a complex whole. As used herein, the term "sub-system" means a system that is a component of a larger system.

As used herein, the symbol "(s)" following the name of an item indicates that one or more of the subject items is intended, depending upon the context. As used herein, the expression "and/or" is used to indicate that either the word "and" or the word "or" can be used to connect words, phrases, or clauses.

Throughout the specification, so far as possible, like parts or components will have the same reference numerals; like parts or components may have different reference numerals when required for the sake of clarity.

The desired components of laboratory automation systems can be positioned in numerous arrangements. FIG. 1 illustrates a laboratory automation system that can be modified for use with the system and method described herein. In this figure is shown an arrangement of a track system for enabling the movement of containers containing samples (alternatively referred to herein as "sample containers") and containers containing reagents (alternatively referred to herein as "reagent containers") from an input/output module to one or more short-term storage areas for reagent containers and sample containers. Also shown in this figure is a section for positioning the analytical instruments of the laboratory automation system.

Referring now to FIG. 1, a laboratory automation system 10 comprises a track system 12. As shown in FIG. 1, the track system 12 has a first lane 14 and a second lane 16. The purpose of the first lane 14 is to transport a container holding a sample (alternatively referred to herein as a "sample container") 18 from an input/output module 20 (see FIG. 2) to a sample container queue 22. A sample container 18 can suitably travel over the track system 12 by means of a sample container carrier (not shown). Sample container carriers suitable for transporting sample containers 18 on a lane of a track system are commercially available from suppliers such as, for example, Inpeco S. p. a., Thermo Fisher Scientific, Inc., Beckman Coulter Inc., Lab Interlink, A&T Corporation, Siemens AG, etc. Such a sample container carrier is described, for example, in U.S. Pat. Nos. 5,417,922; 5,427,743; 5,589,137; and 6,343,690, all of which are incorporated herein by reference. The sample containers 18 can be placed in sample container carriers by means of a suitable robotic mechanism (not shown). The sample container carriers travel along the first lane 14 of the track system 12 by means of an endless conveyor belt, or a suitable alternative thereto. Such conveyor belts, and suitable alternatives thereto, are well known to those having ordinary skill in the art. The sample container 18 or adapter sleeve (not shown) can be equipped with a radio frequency identification tag (not shown), which can be used to identify and track a given sample container 18. In an alternative embodiment of a sample container carrier, the sample container carrier can be equipped with adapter sleeves (not shown), which enable the sample container carriers to be the same size as reagent container carriers (not shown) to adapt to sample containers 18 having differing diameters or differing lengths or both of the foregoing.

The purpose of the second lane 16 is to transport a container holding a reagent (alternatively referred to herein as a "reagent container") 30 from the input/output module 20 to a reagent container queue 32. A reagent container 30 can suitably travel over the track system 12 by means of a reagent container carrier (not shown). A representative example of a reagent container suitable for this purpose is commercially available from Nittobo Boseki Co., Ltd. and Rexam PLC. Such a reagent container is described, for example, in U.S. Pat. Nos. 6,074,615 and 6,555,062, both of which are incorporated herein by reference. The reagent containers 30 can be placed in reagent container carriers by means of a suitable robotic mechanism (not shown). The reagent container carriers travel along the second lane 16 of the track system 12 by means of an endless conveyor belt, or a suitable alternative thereto. Such conveyor belts, and suitable alternatives thereto, are well known to those having ordinary skill in the art. The reagent container 30 can be equipped with a radio frequency identification tag (not shown), which can be used to identify and track a given reagent container 30. It is also possible to use the same lane of the track system 12 to transport sample container carriers and reagent container carriers, as well as to use separate lanes for the sample container carriers and the reagent container carriers. The use of the same lane for both sample container carriers and reagent container carriers could reduce the cost of the track system 12. In addition, the use of the same lane for both sample container carriers and reagent container carriers allows sample container carriers and reagent container carriers to be of the same size.

Adjacent to the track system 12 is at least one analysis section 60 of the laboratory automation system 10. Depending upon the size of the track system 12, more than one analysis section 60 can be employed. The analysis section 60 has four major sub-sections, namely a sub-section 62 for retaining samples and reagents that are to be used in the assays, a sub-section 64 for retaining disposable components for the equipment needed to introduce and manipulate samples and reagents into reaction vessels, e.g., micro-well plates, a sub-section 66 for supporting instruments needed to carry out immunoassays, and a sub-section 68 for supporting instruments needed to carry out clinical chemistry assays. Sub-section 66 is not required to be directly accessible to an aspirating/dispensing device and can utilize kitted micro-well plates. Sub-section 68 generally requires an aspirating/dispensing device that has direct access to micro-well plates. Micro-well plates, and the positions thereof, are designated by the letter "P".

The sub-section 62 of the analysis section 60 is preferably elevated to, a level sufficient to accommodate a radio frequency identification reader (not shown) for reading information from radio frequency identification tags 26, 36. Such a radio frequency identification reader is described in U.S. application Ser. No. 11/495,430, filed Jul. 28, 2006, entitled SYSTEM FOR TRACKING VESSELS IN AUTOMATED LABORATORY ANALYZERS BY RADIO FREQUENCY IDENTIFICATION and U.S. patent application Ser. No. 12/274,479, filed Nov. 20, 2008, and entitled SYSTEM FOR TRACKING VESSELS IN AUTOMATED LABORATORY ANALYZERS BY RADIO FREQUENCY IDENTIFICATION, both of which have previously been incorporated herein by reference.

In the laboratory automation system 10 described herein, samples are shared for both immunoassay and clinical chemistry assay technologies. The samples can be transported to the sub-section 62 of the analysis section 60 by the track system 12 of the laboratory automation system 10 to minimize the storage of samples on the analysis section 60 of the laboratory automation system 10 and to automate retest and/or reflex testing. Alternatively, the samples can be positioned at the sub-section 62 of the analysis section 60 by other means, such as, for example, manually or, if desired, by a robotic mechanism (not shown). As discussed previously, samples can be transferred to the analysis section 60 of the laboratory automation system 10 by means of a sample container carrier 24 or by means of trays 38 that support sample containers 18. A typical sample container tray 38 can hold up to five (5) sample containers 18, a row of sample container trays can typically comprise up to three (3) sample container trays 38, and the sub-section 62 can typically hold up to twelve (12) sample container trays. While the area of the sub-section 62 of the analysis section 60 allocated for sample containers 18 is not critical, it can be seen that up to sixty (60) sample containers 18 can be stored in the sub-section 62. However, more than sixty sample containers 18 can be stored in sub-section 62 of the analysis section 60, if the dimensions of the analysis section 60 are increased.

The sub-section 62 of the analysis section 60 provides sufficient space for temporary storage for reagent containers 30 for clinical chemistry assays, temporary storage of reagent containers 30 for immunoassays, along with equipment for stirring reagents for immunoassays, and temporary storage of sample containers 18. The sub-section 62 can be designed to include reagent containers 30 for clinical chemistry assays only, reagent containers 30 for immunoassays only, or a combination of reagent containers 30 for both types of assays. The sub-section 62 is preferably equipped to provide refrigeration and evaporation control for the reagents and the samples.

The individual reagent containers 30 for clinical chemistry assays and the individual reagent containers 30 for immunoassays can be removed from reagent container carriers, inserted at the appropriate locations of sub-section 62 of the analysis section 60 by means of a robotic system, wherein gripping devices 92 can be affixed to a device 94 that can aspirate and dispense liquids, hereinafter alternatively referred to as an aspirating/dispensing device 94. The aspirating/dispensing device 94 is capable of aspirating liquids from a container and dispensing liquids into a micro-well of a micro-well plate.

Bulk liquids, such as, for example, a pre-trigger solution for certain types of immunoassays, wash buffer, and deionized water, are preferably contained in troughs 116a, 116b, 116c, etc., so that a plurality of pipette tips 110 can aspirate a specific liquid simultaneously. Other bulk liquids can be stored where appropriate. For example, the trigger solution for certain types of immunoassays, which is used in conjunction with the pre-trigger solution, can be stored in a reader, such as, for example, a luminescence reader, whereby the trigger solution is released at the point when the results of the assay are to be read. The trigger solution enables photons to be emitted from the label of the reaction product of the immunoassay within from about 3 to about 5 seconds.

A storage area 120 for pipette tips (both unused pipette tips and pipette tips for reuse) and a temperature controllable micro-well plate rotator 122 or stationary aspirating/dispensing locations 124 are positioned at the sub-section 64 of the analysis section 60. If stationary aspirating/dispensing devices are used, a micro-well plate rotator need not be used.

Racks 126 for disposable pipette tips and containers 128 for solid waste can be located at or near the center of the analysis section 60, thereby minimizing travel distances of the aspirating/dispensing device 94 over the clean laboratory equipment, e.g., pipette tips, micro-well plates, for aspirating/dispensing operations. These racks 126 for disposable pipette tips are used to store disposable pipette tips for immunoassays and clinical chemistry assays prior to the use thereof. Racks 130 for tip combs, i.e., a disposable item used in inverse magnetic particle processing, are used to store tip combs prior to the use thereof. Used tip combs can be disposed of in a rack 132 for used tip combs. "Re-use" racks 134 for pipette tips can be used to store pipette tips allocated to specific reagent containers 30 or bulk liquids in order to reduce the consumption of pipette tips. A rack stacker 136 for disposable tips is capable of storing a large number of racks of disposable tips in a dispenser that dispenses racks of disposable tips. The rack stacker 136 can be an elongated container wherein a spring or motor drive urges the stored racks toward the surface of the analysis section 60. Other "re-use" racks (not shown) for pipette tips can be used to store pipette tips allocated to specific samples when those samples are tested in the immunoassay mode and the clinical chemistry assay mode in order to reduce the consumption of pipette tips. A pipette tip can be reused if the pipette tip repeats the use of the same sample or the same reagent, i.e., so long as there is no carryover from another sample or another reagent. After all of the tests for a given sample are complete, the pipette tip for the sample is ejected to solid waste in a container 128 for solid waste located in an appropriate position near the analysis section 60. The aforementioned racks can be designed to be compatible with the expected contents thereof. Such racks are commercially available and are well-known to those of ordinary skill in the art.

A pre-treatment and dilution area is located at the stationary aspirating/dispensing location 124. At this location, if desired, the micro-well plate can be maintained in a stationary position, i.e., incapable of rotation. Pre-treatment steps and/or dilution steps are performed prior to immunoassay processing and clinical chemistry assay processing.

Referring now to FIGS. 1, 5, and 6, an immunoassay processor 140 is positioned at the sub-section 66 of the analysis section 60. In FIG. 7, a different type of immunoassay processor is used. This immunoassay processor is designated by the reference numeral 140*a*. More than one immunoassay processor 140 can be utilized. A clinical chemistry assay processor 142 is positioned at the sub-section 68 of the analysis section 60. More than one clinical chemistry assay processor can be utilized. Storage racks 144 for micro-well plates are positioned at or near the sub-section 68 of the analysis section 60. Stackers 146 for micro-well plates are used to store micro-well plates for immunoassays and clinical chemistry assays prior to kitting the micro-well plates for immunoassays or clinical chemistry assays. As indicated previously, the laboratory automation system described herein can function with a clinical chemistry assay processor(s) without any immunoassay processor or can function with an immunoassay processor(s) without any clinical chemistry processor.

The immunoassay processor 140 provides the following functions: incubation of reaction mixtures, mixing of reaction mixtures, separation of components from reaction mixtures, washing of reaction product(s), and release of label to enable reading of the results of immunoassays. An immunoassay processor 140 that can be modified for use herein is a KingFisher™ magnetic particle processor, commercially available from Thermo Fisher Scientific, Inc., Waltham, Mass., and described in U.S. application Ser. No. 11/923,828, filed Oct. 25, 2007, and entitled METHOD OF PERFORMING ULTRA-SENSITIVE IMMUNOASSAYS, incorporated herein by reference.

A luminescence reader 150 separate from the immunoassay processor 140 is positioned at the sub-section 68 of the analysis section 60 to read the results of the immunoassay from the micro-well plates after the reaction mixtures are processed. The micro-well plates can be moved from the immunoassay processor 140 to the luminescence reader 150 by means of a conveyor belt 151. Alternatively, the micro-well plates can be moved from the immunoassay processor 140 to the luminescence reader 150 by means of a robotic mechanism.

The items shown in FIG. 1 are described in greater detail in U.S. patent application Ser. No. 12/257,495, filed Oct. 24, 2008, and entitled AUTOMATED ANALYZER FOR CLINICAL LABORATORY, incorporated herein by reference.

Figure 2:
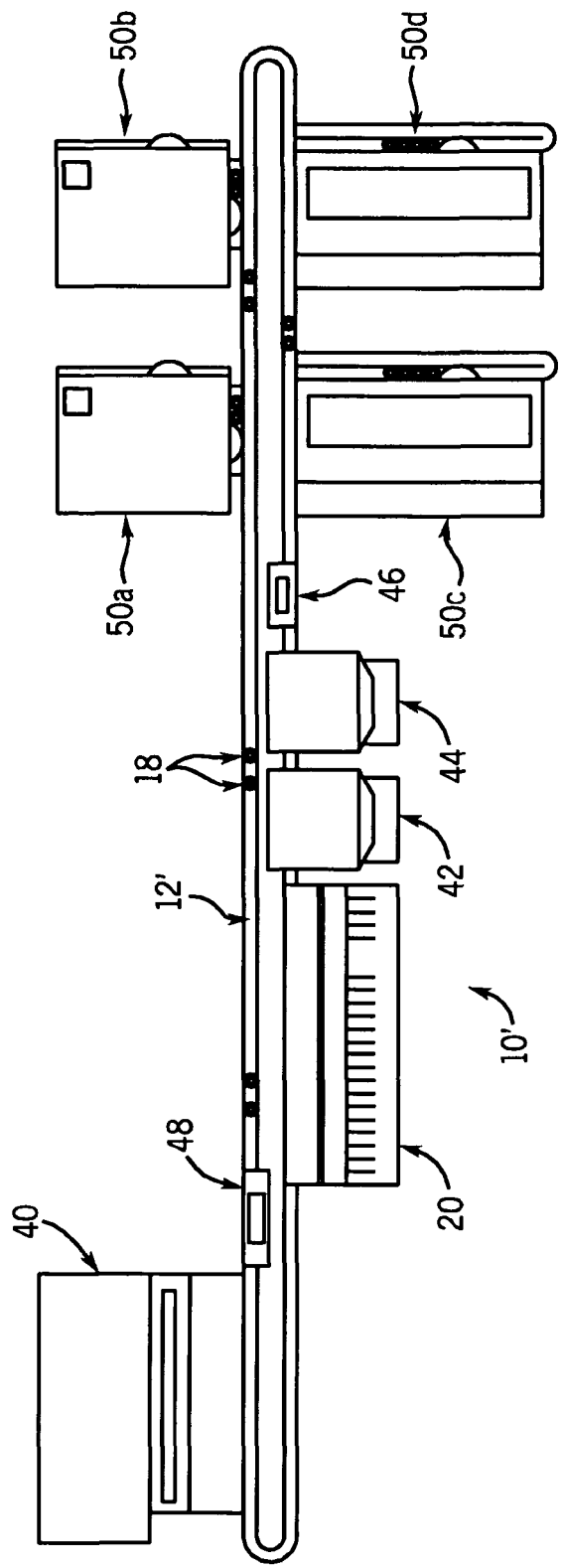
FIG. 2 is a schematic diagram illustrating a laboratory automation system currently available.

FIG. 2 illustrates other conventional components of a laboratory automation system that can be placed around the track arrangement. These components include a first immunoassay analyzer 50*a*, a second immunoassay analyzer 50*b*, a first clinical chemistry analyzer 50*c*, and a second clinical chemistry analyzer 50*d*. The disclosure described herein can utilize different types of immunoassay analyzers and different types of clinical chemistry analyzers. The items shown in FIG. 2 are described in greater detail in U.S. patent application Ser. No. 12/257,495, filed Oct. 24, 2008, and entitled AUTOMATED ANALYZER FOR CLINICAL LABORATORY, previously incorporated herein by reference.

Automated clinical analyzers associated with the laboratory automation systems typically employ aspirating/dispensing devices wherein a pipette (or pipettes) of the aspirating/dispensing device can be moved in three dimensions, i.e., two dimensions in a horizontal plane (i.e., X and Y) and one dimension vertically (i.e., Z). The remaining components of laboratory automation systems can be placed near to or be connected with the aspirating/dispensing device to enable the pipette (or pipettes) to obtain access to various components of the laboratory automation system. However, not all components require direct access from an aspirating/dispensing device.

Depending on the desired capabilities of the laboratory automation system, laboratory automation sub-systems (e.g., various diagnostic assay technologies) can added to or subtracted from the aspirating/dispensing device. In addition, multiple sub-systems can be added to the laboratory automation system to increase throughput, e.g., one or more immunoassay sub-systems can be added to an immunoassay sub-system to increase throughput of immunoassays, or one or more clinical chemistry assay sub-systems can be added to a clinical chemistry assay sub-system to increase throughput of clinical chemistry assays.

A typical system for managing inventories of reagents includes an operator interface for the loading of boxes of reagents and other supplies, a radio frequency identification system for identification and tracking of reagents and other consumable items, robotic mechanisms for loading reagents and other consumable items onto the track system of a laboratory automations system and removing reagents and other consumable items from the track system of a laboratory automation system, de-capping equipment, refrigeration equipment, and information technology connections to clinical analyzers and vendors of reagents and other consumable items. The information technology connections combine to form a laboratory information system.

A system for managing the inventory of reagents can be designed to place reagent containers 30 into reagent container carriers, after which placement, these reagent container carriers can be routed to the analysis section 60 of the laboratory automation system 10, where they can be diverted into the correct local queue 32. Such placement can be effected by a robotic mechanism (not shown), which has the capability of picking up a reagent container 30 from a storage location near the track system 12 and placing the reagent container 30 on a reagent container carrier. Similarly, a system for providing the samples can be designed to place sample containers 18 into sample container carriers (not shown) or reagent container carriers (not shown) having adapter sleeves (not shown), after which placement, these sample container carriers can be routed to the analysis section 60 of the laboratory automation system 10, where they can be diverted into the correct local queue 22. Such placement can be effected by a robotic mechanism (not shown), which has the capability of picking up a sample container 18 from a storage location near the track system 12 and placing the sample container 18 on a sample container carrier (not shown) or a reagent container carrier (not shown) having an adapter sleeve (not shown).

A plurality of smart refrigerators and a plurality of clinical analyzers can be managed by one controller for the system for managing inventories of reagents. This architecture allows the greatest level of flexibility to comprehend small or large reagent inventories, depending upon the needs of a laboratory.

Figure 3:
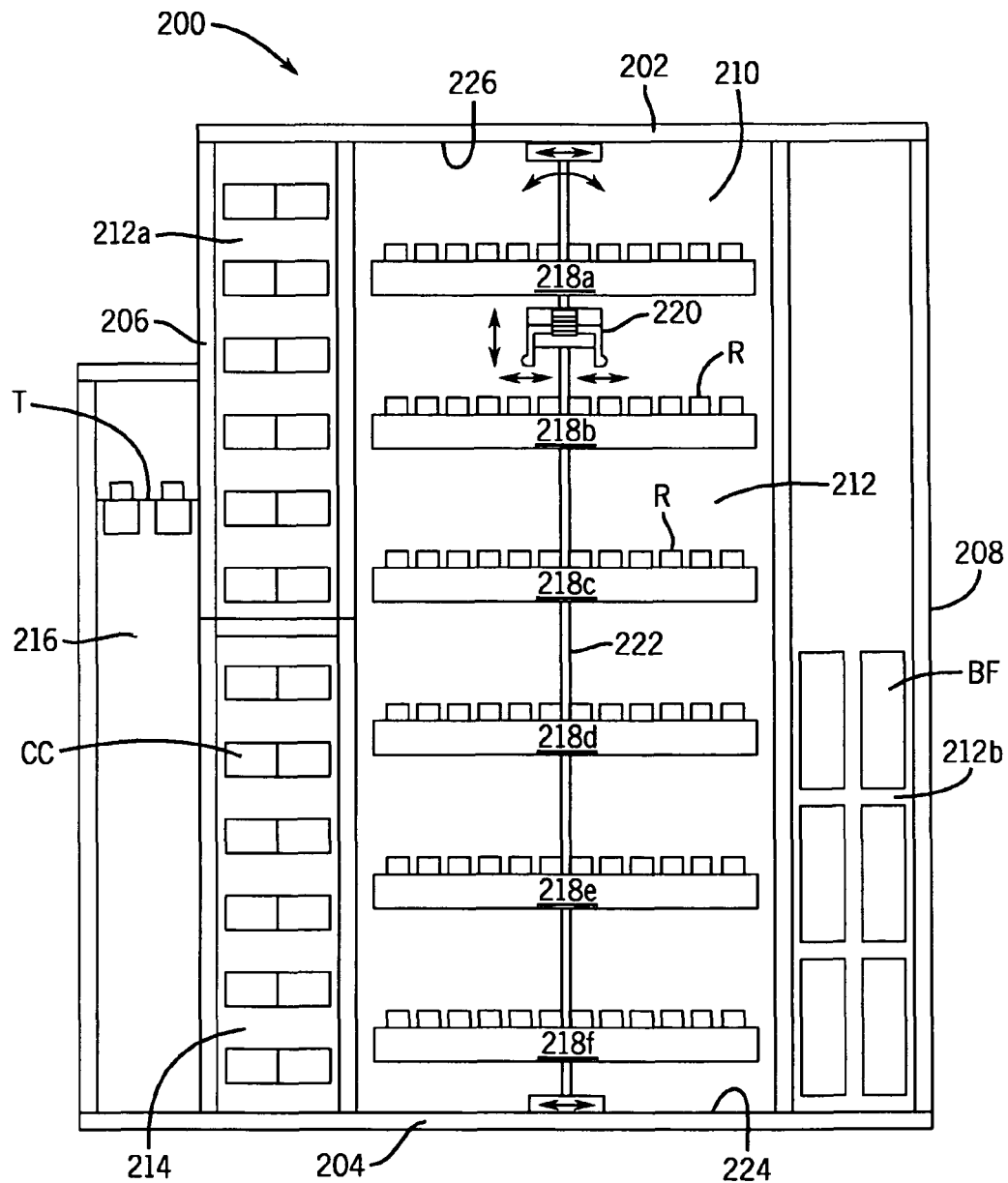
FIG. 3 is a side view in elevation of a schematic diagram illustrating several areas of the refrigerator described herein.

FIG. 3 shows a smart refrigerator 200. The smart refrigerator 200 has a top wall 202, a bottom wall 204, a first sidewall 206, a second sidewall 208, and a rear wall 210. The smart refrigerator also has a door that forms a front wall that is parallel to the rear wall 210. In the smart refrigerator 200 shown in FIG. 3, the door can be a sliding door or a hinged door. The door can be made of a transparent material, such as for example, plastic, shatter-resistant glass. The door can also be made of a material that is not transparent. The door can be opened to enable an operator to insert (a) one or more packages, each package containing one or more reagent containers or (b) one or more individual reagent containers without the package in which they were shipped to the user.

The smart refrigerator 200 has two internal compartments. The refrigeration compartment is designated by the reference numeral 212. The freezer compartment is designated by the reference numeral 214. Calibrators and controls "CC" can be stored in a sub-compartment 212a of the refrigeration compartment 212. Bulk fluids "BF", which are typically in liquid form and are alternatively referred to as bulk liquids, can be stored in a sub-compartment 212b of the refrigeration compartment 212. Reagents "R" for specific assays can be stored in a third sub-compartment of the refrigeration compartment 212. As shown in FIG. 3, the third sub-compartment of the refrigeration compartment 212 is located between the sub-compartment 212a and the sub-compartment 212b. An input/output module 216 is positioned adjacent to the smart refrigerator 200. As shown in FIG. 3, the input/output module 216 is connected to a track "T", which leads to a laboratory automation system, which is shown in FIGS. 1 and 2. The freezer compartment is preferably maintained at a temperature ranging from about −30° C. to about −20° C. The refrigeration section is preferably maintained at a temperature ranging from about 2° C. to about 8° C. Some bulk liquids require refrigeration. The open storage area in the upper portion of the sub-compartment 212b provides storage space for whatever the customer desires to store. Typical dimensions of the smart refrigerator are 50 inches in width by 60 inches in height by 24 inches in depth. The third sub-compartment of the refrigeration compartment 212, which, as stated previously, is located between the sub-compartment 212a and the sub-compartment 212b, includes a plurality of shelves 218a, 218b, 218c, 218d, 218e, and 218f. It should be noted that the smart refrigerator 200 can employ more than six (6) shelves or fewer than six (6) shelves.

A robotic system can be employed to retrieve a given reagent container from a given position on a given shelf of the sub-component 212c of the smart refrigerator 200. The robotic system can comprise a XYZ robot in a gantry system. The XYZ robot has grippers for grasping containers. The grippers should be capable of gripping any type of container that is to be stored in the smart refrigerator. This robotic system grips and elevates containers from the refrigerated area(s) and places the containers on either a reagent carrier, for manual transportation by a human operator, or to a transportation component of a laboratory automation system, for automated transport of the container to a clinical analyzer. Robotic systems suitable for use herein can be manufactured by one of ordinary skill in the art, e.g., vendors of robotic systems.

Referring again to FIG. 3, a robotic gripping device 220 is capable of moving vertically by means of a threaded screw 222. Attached to the robotic gripping device 220 is a nut (not shown) that enables the robotic gripping device 220 to move vertically along the threaded screw 222. Movement of the nut can be actuated by a motor (not shown), typically a stepper motor. The robotic gripping device 220 is further capable of moving in a horizontal direction along tracks 224, 226, which are dedicated to the robotic gripping device 220. The robotic gripping device 220 can be designed to have features to enable telescoping movement and rotational movement. The telescoping feature enables the robotic gripping device 220 to have the reach thereof extended or retracted. The rotational feature facilitates the gripping, raising, lowering, and placing of micro-well plates in positions desired. The robotic gripping device 220 is capable of retrieving a reagent container from any compartment or sub-compartment of the smart refrigerator 200 and placing the reagent container on the input/output module 216 or on the track "T" leading to a laboratory automation system. The robotic gripping device 220 can obtain access to the input/output module 216 or to the track "T" leading to a laboratory automation system by way of an aperture (not shown) formed in the first sidewall 206. If necessary, additional apertures can be formed in any other barriers between the robotic gripping device 220 and the input/output module 216 and the track "T" leading to a laboratory automation system. The aperture(s) can be opened and closed by means of a door, which door can be opened or closed when required by a controller. Robotic gripping devices are discussed in greater detail in U.S. patent application Ser. No. 12/257,495, filed Oct. 24, 2008, and entitled AUTOMATED ANALYZER FOR CLINICAL LABORATORY, previously incorporated herein by reference.

The mechanical and chemical components of the smart refrigerator are commercially available and can readily be obtained from vendors.

Figure 4A:
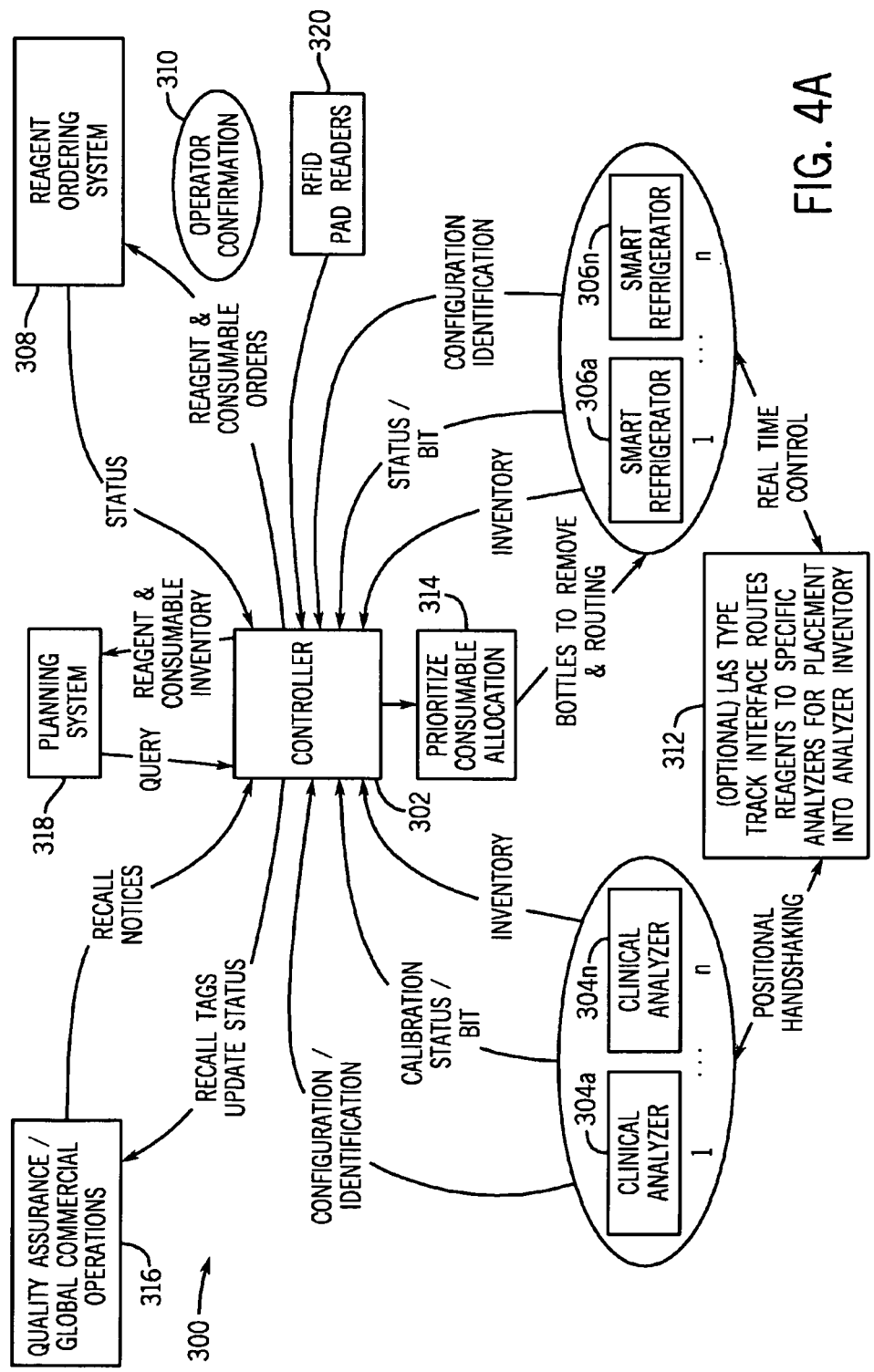
FIG. 4A is a schematic diagram illustrating the interfaces between the controller of the system for managing inventories of reagents, various clinical analyzers, and refrigerators.

Referring now to FIG. 4A, the system 300 for managing inventories of reagents has a central controller 302 that interfaces with a plurality of clinical analyzers 304a through 304n, inclusive, and a plurality of smart refrigerators 306a through 306n, inclusive.

The controller 302 for the system 300 for managing inventories of reagents receives the following types of information from at least one clinical analyzer 304a through 304n, inclusive:

(a) configuration information for the clinical analyzer
(b) identification information for the clinical analyzer
(c) calibration status of the clinical analyzer
(d) built-in tests (BIT) to indicate a functional status of the clinical analyzer
(e) inventory, information for the clinical analyzer The controller 302 for the system 300 for managing inventories of reagents receives the following types of information from at least one smart refrigerator 306a through 306n, inclusive:

(a) configuration information for the smart refrigerator
(b) identification information for the smart refrigerator
(c) calibration status of the smart refrigerator
(d) built-in tests (BIT) to indicate a functional status of the smart refrigerator
(e) inventory information for the smart refrigerator The controller 302 for the system 300 for managing inventories of reagents provides assignment information and routing information to the smart refrigerator(s) 306a through 306n, inclusive.

A reagent ordering system 308 operated by a supplier interfaces with the controller 302 of the system 300 for managing inventories of reagents, which is operated by the customer. The operator typically confirms the orders for reagents and other consumable items 310. However, the system for managing inventory of reagents is capable of creating and confirming the orders for reagents and other consumable items from a supplier without the intervention of the operator.

Other systems that are able to communicate with the system for managing the inventory of reagents are (a) a system for prioritizing the use of consumable items 314, such as, for example, reagents, (b) a system for quality assurance and global commercial operations 316, and (c) a system for the planning of inventory of reagents 318. A radio frequency identification pad reader 320 can be used as a device to input data or as an alternative to the smart refrigerator.

Figure 4B:
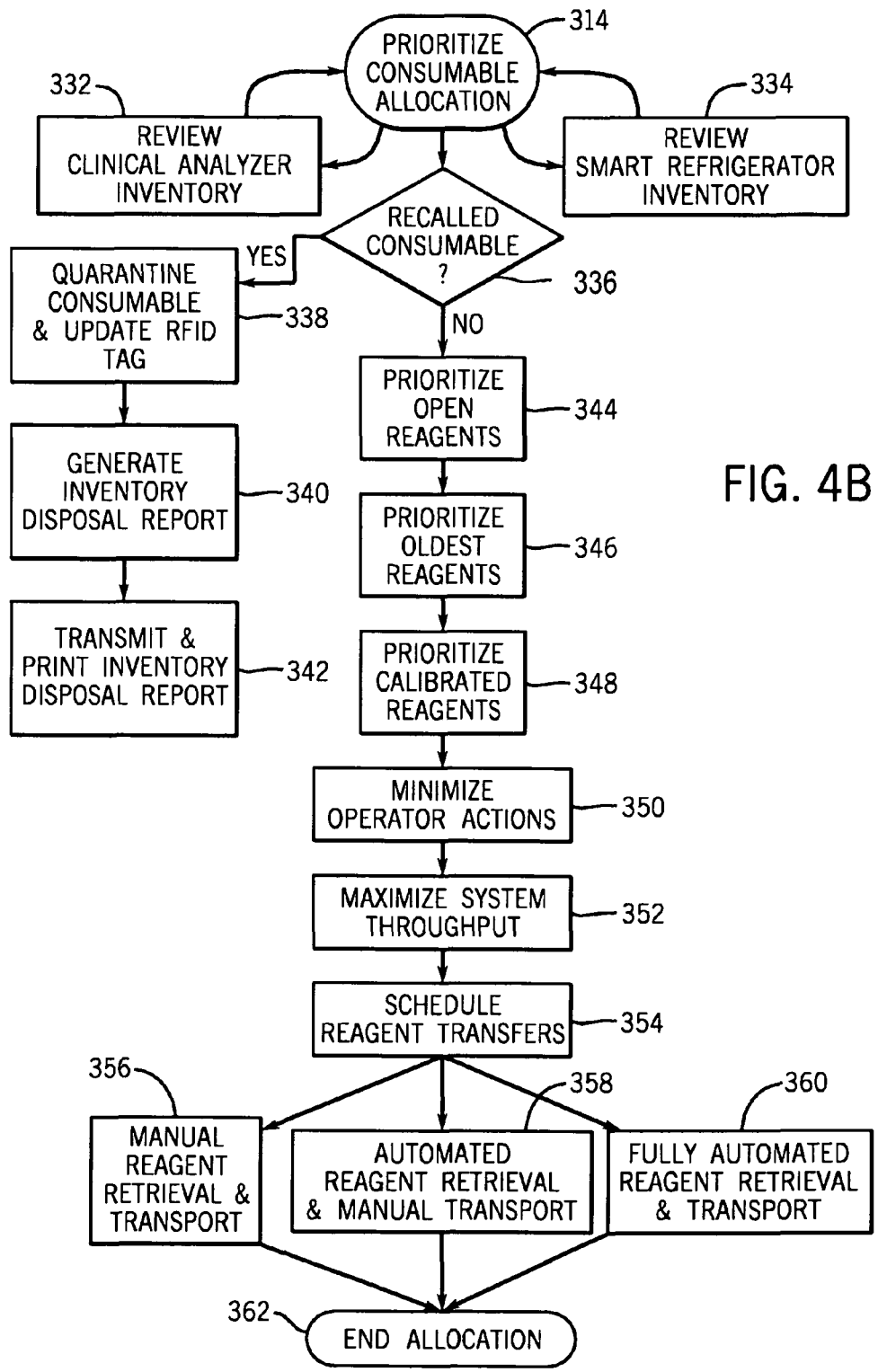
FIG. 4B is a flowchart illustrating a process for prioritizing the allocation of consumable items.

The system for prioritizing the use of consumable items 314 is illustrated by the flow chart in FIG. 4B. The software for managing of inventories of reagents can review inventory of reagents in the clinical analyzer(s) (step 332) and can review inventory of reagents in the smart refrigerator(s) (step 334). In step 336, the system for prioritizing the use of consumable items determines whether the consumable item has been recalled. If the consumable item has been recalled, the consumable item is quarantined and the radio frequency identification tag is updated to account for this step (step 338). Then an inventory disposal report can be generated (step 340). The inventory disposal report can then be transmitted and printed to the appropriate recipient (step 342). If the consumable item has not been recalled, or if the consumable item has been recalled but is still considered to be viable, reagents in open containers are prioritized (step 344). Then the oldest reagents, i.e., reagents closest to reaching expiration dates, are prioritized (step 346). Then reagents that have been calibrated are prioritized (step 348). Then the system for prioritization determines a sequence for minimizing the actions required by an operator (step 350). Then the system for prioritization determines a sequence for maximizing the throughput of the system (step 352). Then transfers of reagents are scheduled (step 354). Transfers of reagents can be carried out in one of three ways—(a) manual retrieval and transport of reagents (step 356); (b) automated retrieval of reagents and manual transport of reagents (step 358); (c) fully automated retrieval and transport of reagents (step 360). At this point (step 362), the prioritization algorithm is complete.

The system for quality assurance/global commercial operations 316 can issue recall notices for reagents. The system for planning 318 can query the system for managing inventory of reagents 300. Upon receiving a query, the system for managing inventory of reagents 300 can provide the inventory of reagents and other consumables to the system for planning 318.

A laboratory automation system, which was described previously, interfaces with a routing system 312, such as, for example, a track system. The routing system 312 routes reagents to specific clinical analyzers for placement into analyzer inventory. The laboratory automation system is optional, i.e., the system for managing inventory of reagents can function in an environment wherein a laboratory automation system is not used.

Real time control between a laboratory automation system and a smart refrigerator allows the laboratory automation system and the smart refrigerator to coordinate their functions. For example, when a reagent container is positioned by the laboratory automation system for a set of assays, a message is sent to the smart refrigerator. Then the smart refrigerator provides the reagent container and sends a message to the laboratory automation system to move the reagent container to the appropriate clinical analyzer. Real time control is further described in Stewart, Introduction to Real Time, Embedded Systems Design—Embedded.com, Nov. 1, 2001, at http://www.embedded.com/story/OEG20011016S0120, incorporated herein by reference.

Positional handshaking between a laboratory automation system and a clinical analyzer allows the laboratory automation system and the clinical analyzer to coordinate their functions. For example, when a sample tube is positioned by the laboratory automation system for an aspirating step, a message is sent to the clinical analyzer. Then the clinical analyzer aspirates the sample and sends a message to the laboratory automation system to move the sample to the next clinical analyzer.

Because of a plurality of package sizes whereby reagents are sold to customers, and the positional requirements for reading radio frequency identification tags on the bottoms of containers, it is necessary to develop carriers for containers and shelves that are capable of being reconfigured. In addition, the method of loading packages should be intuitive and easy for operators to carry out. Packaging can provide several arrays for containers, such as, for example, two rows with two containers in each row, one row with six containers in the row, four rows with two containers in each row, four rows with three containers in each row, four rows with six containers in each row.

Figure 5A:
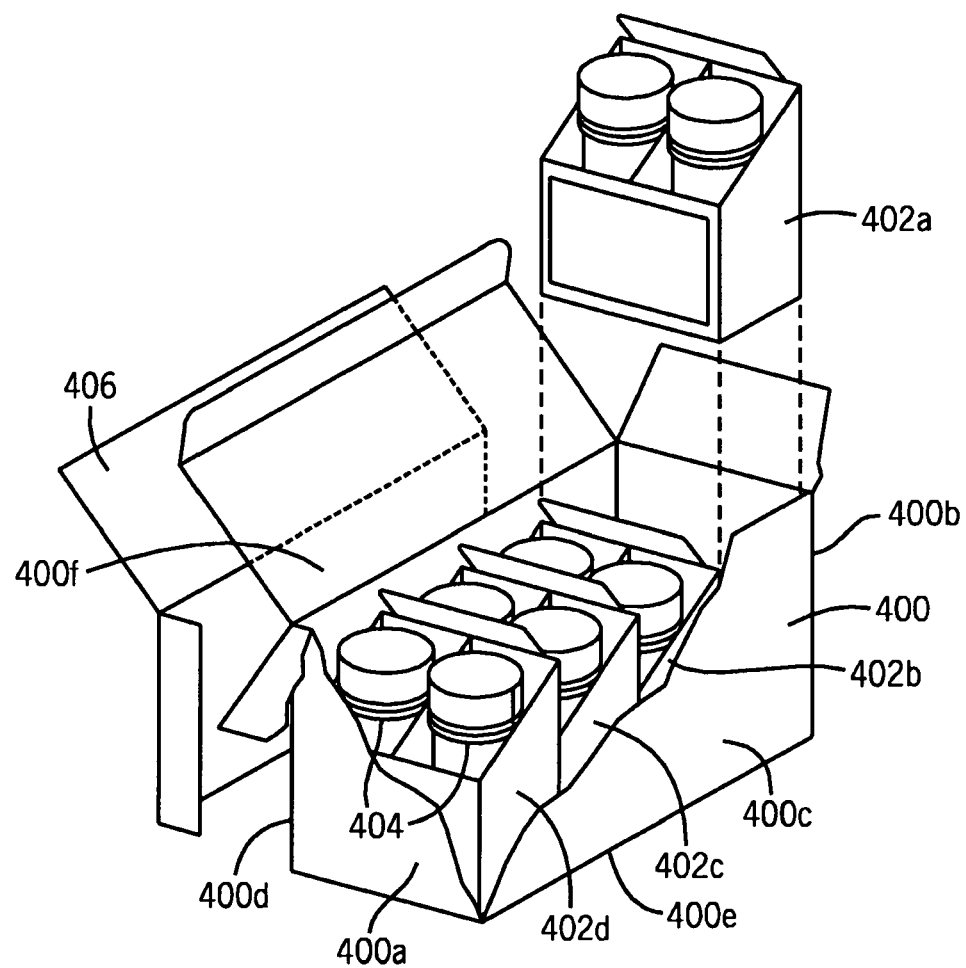
FIG. 5A is a perspective view of a container, i.e., a box, for holding a plurality of reagent containers. In this drawing, it can be seen that the container holds eight reagent containers.
Figure 5B:
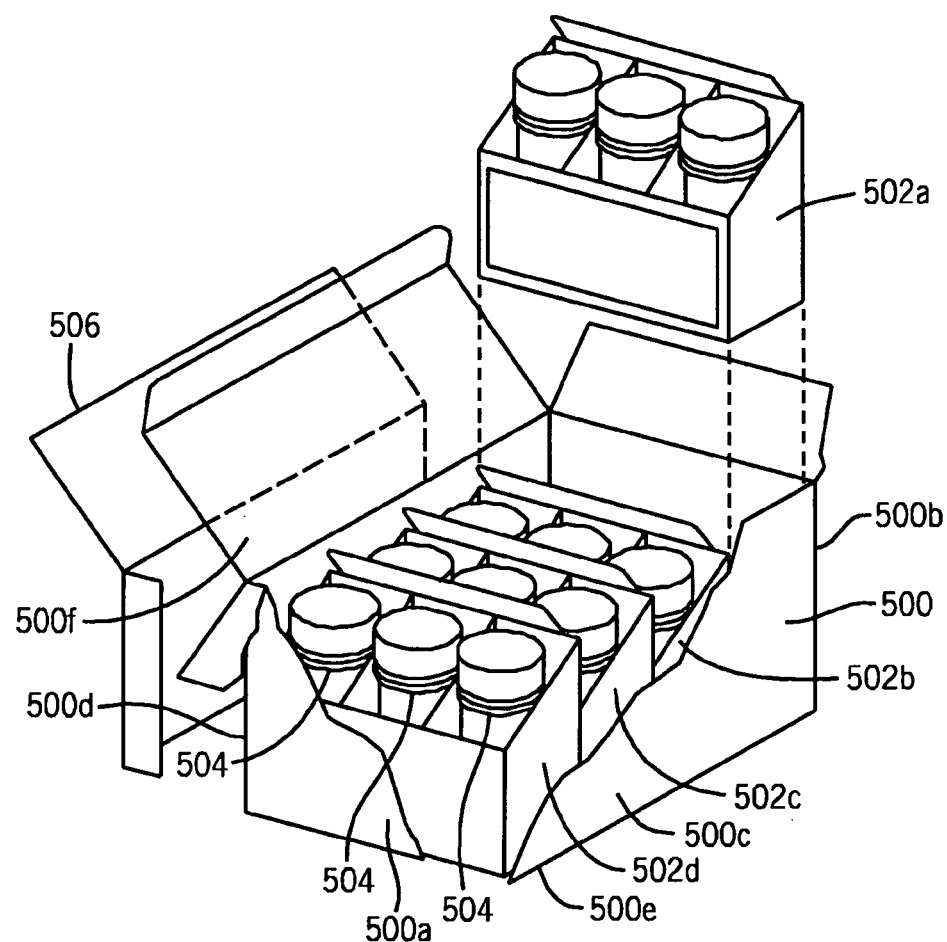
FIG. 5B is a perspective view of a container, i.e., a box, for holding a plurality of reagent containers. In this drawing, it can be seen that the container holds twelve reagent containers.
Figure 5C:
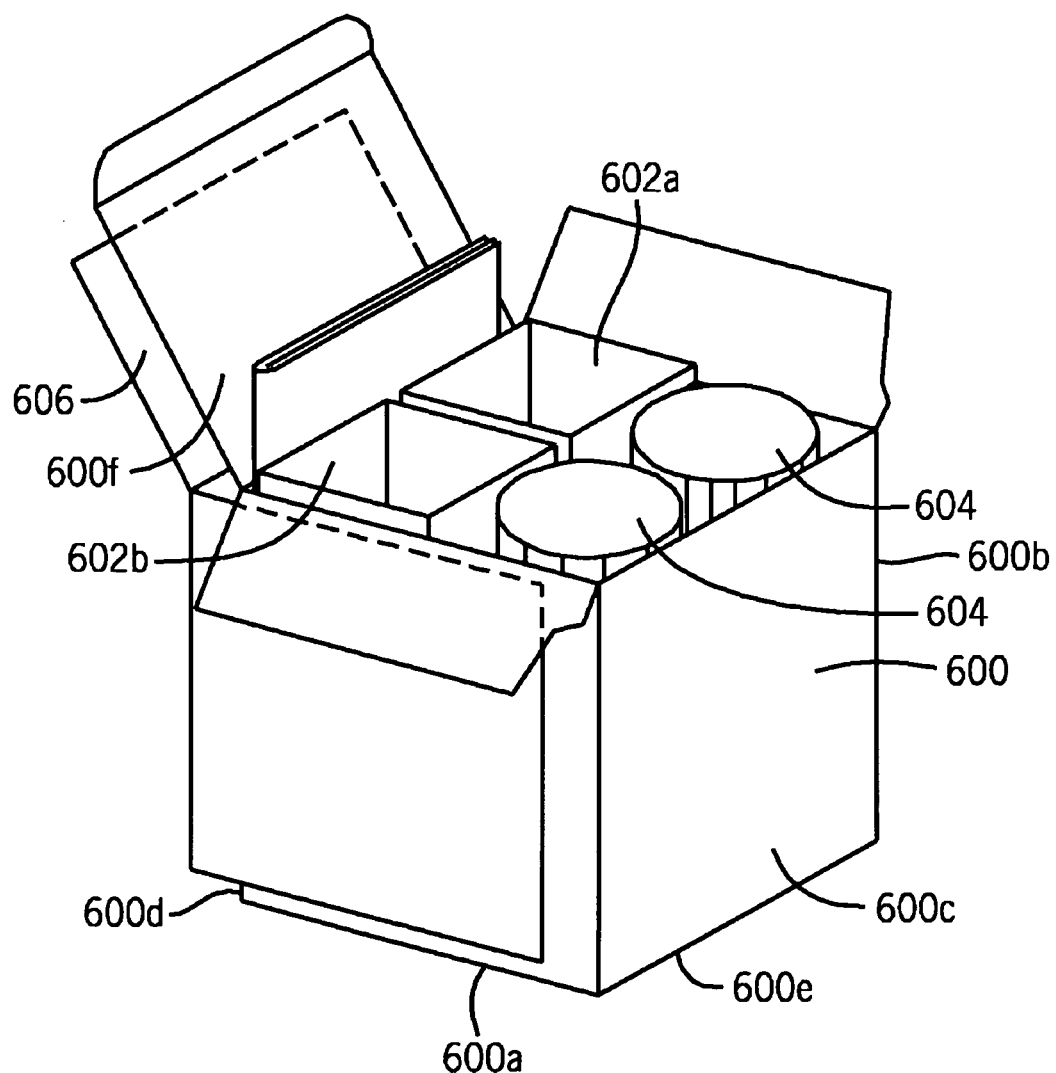
FIG. 5C is a perspective view of a container, i.e., a box, for holding a plurality of reagent containers. In this drawing, it can be seen that the container holds four reagent containers.

FIGS. 5A, 5B, and 5C illustrate varieties of packages for reagents. FIG. 5A is a perspective view of a package 400 for holding eight reagent containers in a 2×4 array. The package 400 contains four smaller packages 402a, 402b, 402c, and 402d. Each of the smaller packages contains two reagent containers 404 in a 2×1 array. The package 400 has a front wall 400a, a rear wall 400b, a first side wall 400c, a second side wall 400d, a bottom wall 400e, and a top wall 400f. The top wall 400f is joined to the second side wall 400d, but is not joined to the first side wall 400c. The top wall 400f is rotatable about the edge of the second side wall 400d to enable an XYZ robot to have access to the containers 404. Each package 402a, 402b, 402c, and 402d has a front wall, a rear wall, a first side wall, a second side wall, and a bottom wall. Each package 402a, 402b, 402c, 402d does not have a top wall. A label 406 is attached to the exterior of the package 400 so that the operator or a bar code reader can identify the contents of the package 400.

FIG. 5B is a perspective view of a package for holding eight reagent containers in a 3×4 array. The package 500 contains four smaller packages 502a, 502b, 502c, 502d. Each of the smaller packages contains three reagent containers 504 in a 3×1 array. The construction of the package 500 is substantially similar to the construction of the package 400, and the construction of the packages 502a, 502b, 502c, 502d is substantially similar to the construction of the packages 402a, 402b, 402c, 402d, respectively. The only significant difference between the package 500 and the package 400 and the packages 502a, 502b, 502c, 502d and the packages 402a, 402b, 402c, and 402d, respectively, is the size, on account of the fact that the packages in FIG. 5B contain twelve (12) reagent containers and the packages in FIG. 5A contain eight (8) reagent containers. The package 500 has a front wall 500a, a rear wall 500b, a first side wall 500c, a second side wall 500d, a bottom wall 500e, and a top wall 500f. The top wall 500f is joined to the second side wall 500d, but is not joined to the first side wall 500c. The top wall 500f is rotatable about the edge of the second side wall 500d to enable an XYZ robot to have access to the containers 504. Each package 502a, 502b, 502c, and 502d has a front wall, a rear wall, a first side wall, a second side wall, and a bottom wall. Each package 502a, 502b, 502c, 502d does not have a top wall. A label 506 is attached to the exterior of the package 500 so that the operator or a bar code reader can identify the contents of the package 500.

FIG. 5C is a perspective view of a package for holding four reagent containers in a 2×2 array. The package 600 contains two inserts 602a, 602b. The package 600 contains two reagent containers 604. The inserts 602a, 602b function to allow the reagent containers 604 to be removed from the package 600 as a set, while maintaining proper spacing between the containers 604. The construction of the package 600 is substantially similar to the construction of the package 400 and to the construction of the package 500. The only significant difference between the package 600 and the package 400 and the package 500 is the size, on account of the number of containers to be supplied in each of the packages. The package 600 has a front wall 600a, a rear wall 600b, a first side wall 600c, a second side wall 600d, a bottom wall 600e, and a top wall 600f. The top wall 600f is joined to the second side wall 600d, but is not joined to the first side wall 600c. The top wall 600f is rotatable about the edge of the second side wall 600d to enable an XYZ robot to have access to the containers 604. A label 606 is attached to the exterior of the package 600 so that the operator or a bar code reader can identify the contents of the package 600.

The shapes of the containers for reagents are not critical. In general, reagents are typically provided in cylindrical-shaped containers. The shapes of the packages for the containers are not critical. In general however, the packages are in the form of six-sided boxes. The packages typically have a bottom, which is generally in the form of a parallelogram, a top, which is generally in the form of a parallelogram, and four sides, each of which is generally in the form of a parallelogram. Any type of reagent suitable for use in clinical analyzers can be contained in the containers. Representative examples of reagents suitable for use herein include reagents that can be used in the ARCHITECT® immunoassay analyzers and the ARCHITECT® clinical chemistry analyzers. These reagents are commercially available from Abbott Laboratories, Abbott Park, Ill. USA.

To accommodate various sizes of packages, yet precisely position the containers, and radio frequency identification tags, over radio frequency identification interrogators, dividers configurable by operators can be positioned over the antenna boards located in smart refrigerators. The dividers can be made of a polymeric material, preferably a polymeric material that is resistant to being degraded by reagents. The dimensions of the dividers are not critical. A divider suitable for use herein has a width of approximately ¼ inch and a height of approximately ½ inch. Preferably the dividers have features that enable a plurality of dividers to be locked together. The shelves in the smart refrigerator are the type of shelves present in commercially available refrigerators. Such refrigerators have chrome-plated, welded, wire shelves. In addition, once a shelf is configured, loading reagent packages will be intuitive and easy.

As packages change, shelves can be re-figured as required. The only "assumed" feature of this reagent packaging is that the center to center distance for each container is the same, to match the center to center spacing of the radio frequency identification interrogators on the shelf of the smart refrigerator.

FIGS. 6A, 6B, 6C, 6D, 6E, 6F, 6G, and 6H show varieties of configurations for the shelves of smart refrigerators. For simplification of loading the smart refrigerator, each shelf can be configured for a different size of reagent package. However, for the highest density, a given shelf can be configured for any combination of reagent packages that the customer requires.

Figure 6A:
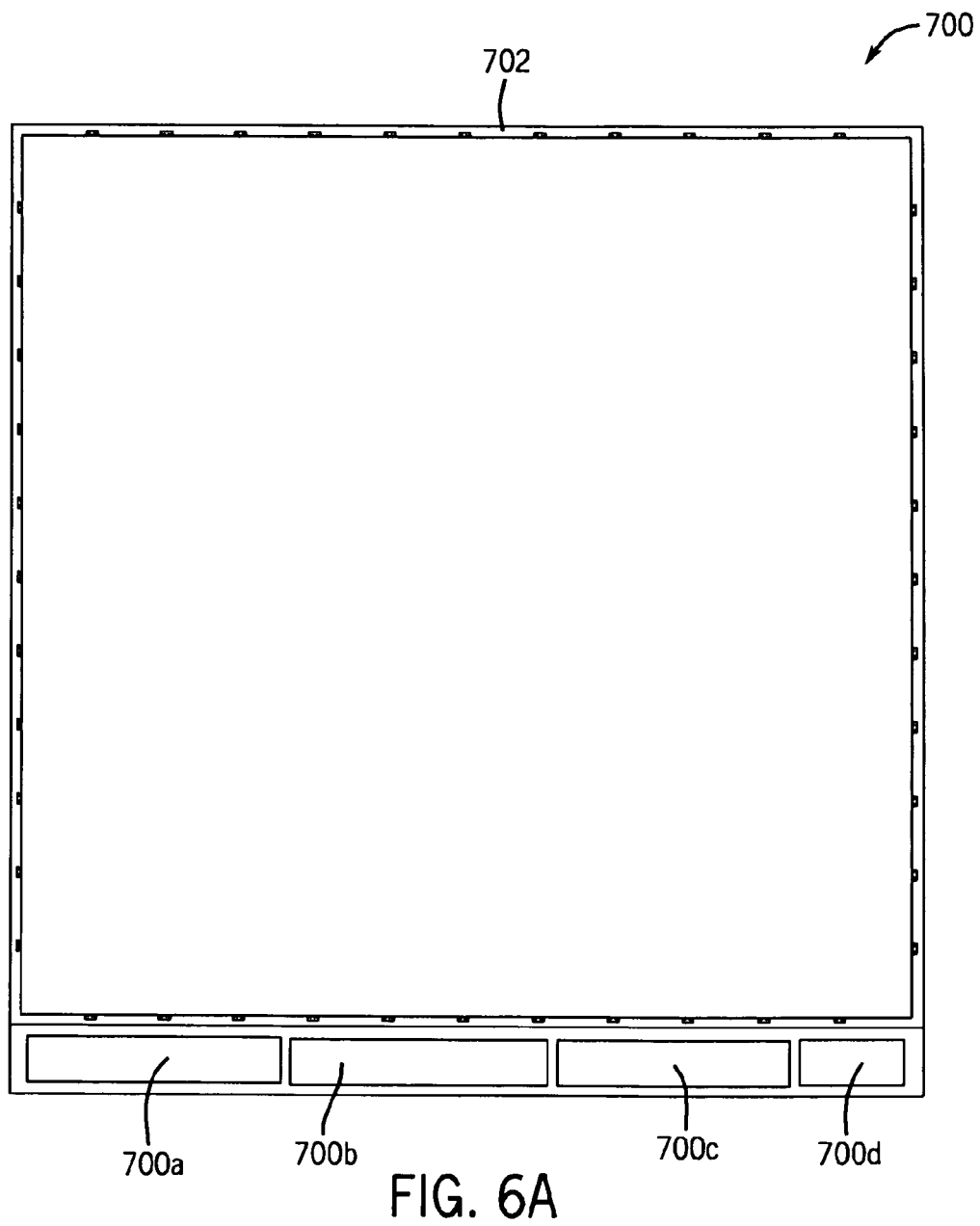
FIG. 6A is a top plan view of an antenna board suitable for use with the system for managing the inventory of reagents described herein.
Figure 7:
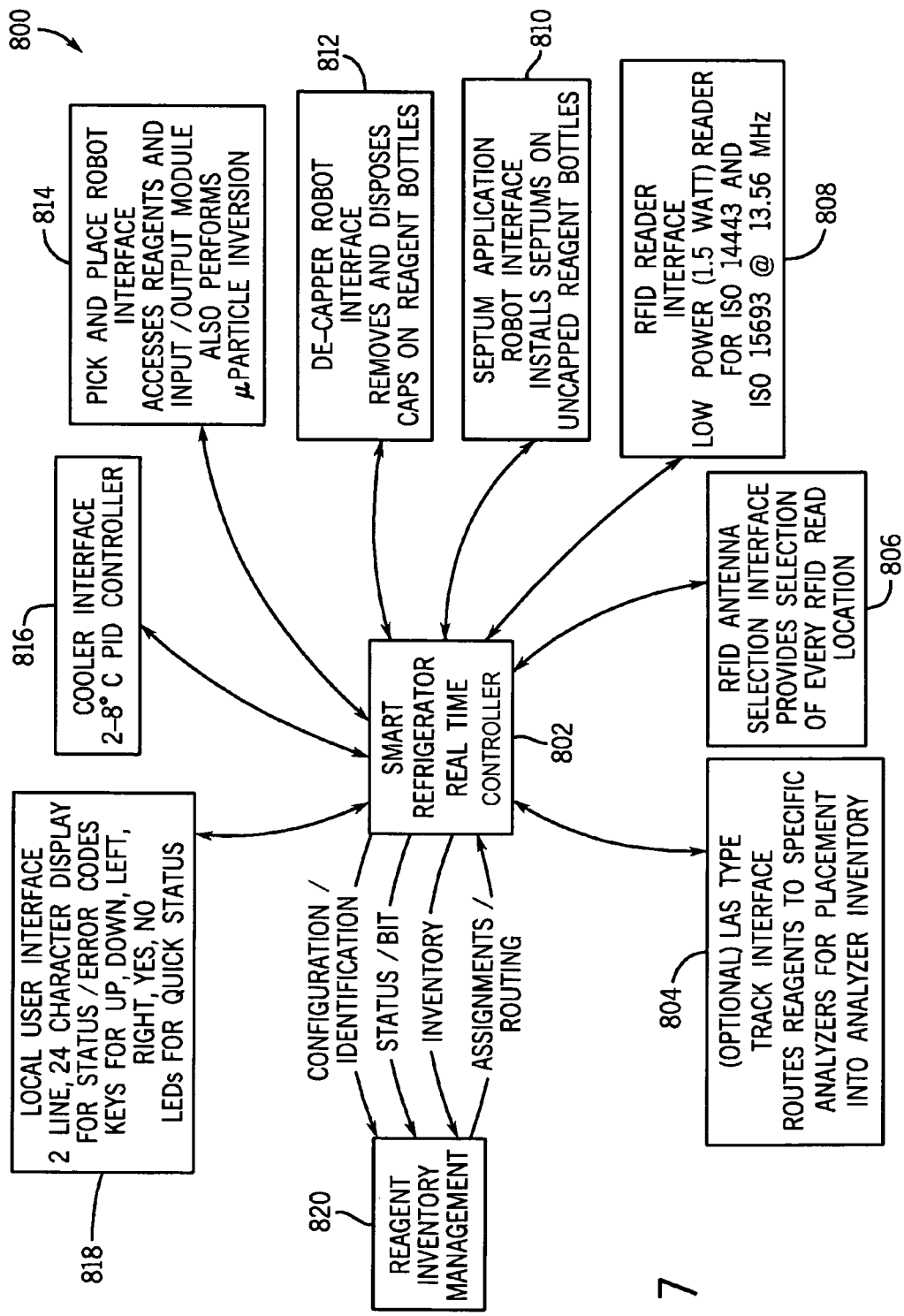
FIG. 7 is a block diagram illustrating the functions and sub-systems of the smart refrigerator described herein and the system for managing the inventory of reagents described herein.

FIG. 6A is a top plan view of an antenna board 700 suitable for use with the smart refrigerator described herein. Typical dimensions are 22 inches by 24 inches. In addition to the antennas (not shown), the antenna board 700 shown in FIG. 6A comprises 255 channel RF output Mux switch 700a, 255 channel RF input Mux switch 700b, CPU and peripheral logic interface 700c, USB I/F interface 700d. However, the actual design of the antenna board can be modified in order to accommodate other desirable configurations. Overlying the antenna board 700 is a frame 702, the purpose of which will be described below.

Figure 6B:
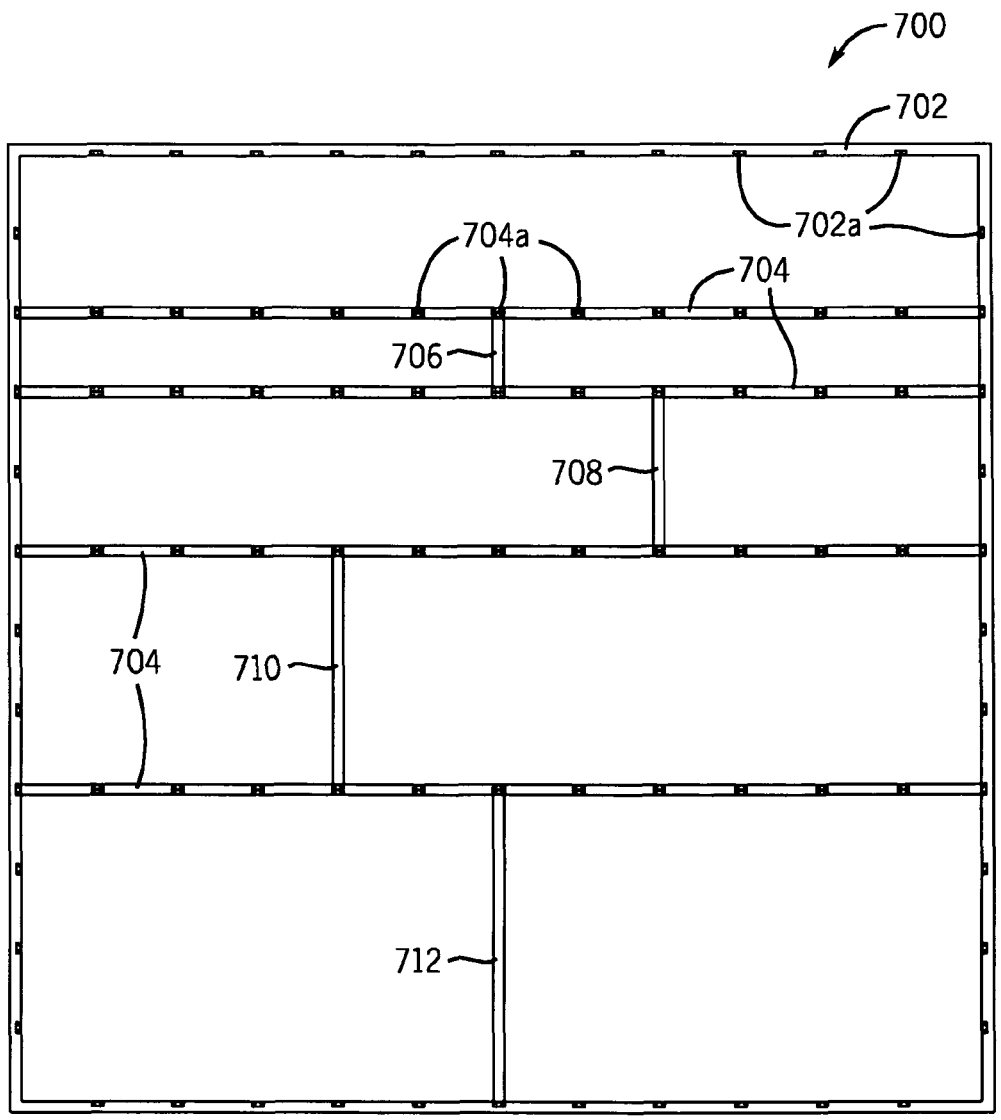
FIG. 6B is a top plan view of a set of dividers that can be placed by an operator to derive a configuration of a shelf capable of receiving and positioning selected reagent kits of various sizes.

FIG. 6B is a top plan view of a frame 702 and a set of elongated dividers 704, 706, 708, 710, and 712 that can be moved about by an operator in order to configure the spaces of a shelf of the smart refrigerator for receiving and positioning reagents kits of various sizes. The frame 702 has a plurality of slots 702a for receiving tabs (not shown) located at the ends of the elongated dividers 704, 706, 708, 710, and 712. The elongated dividers 704 also have a plurality of slots 704a for receiving tabs (not shown) located at the ends of the elongated dividers 706, 708, 710, and 712.

Figure 6C:
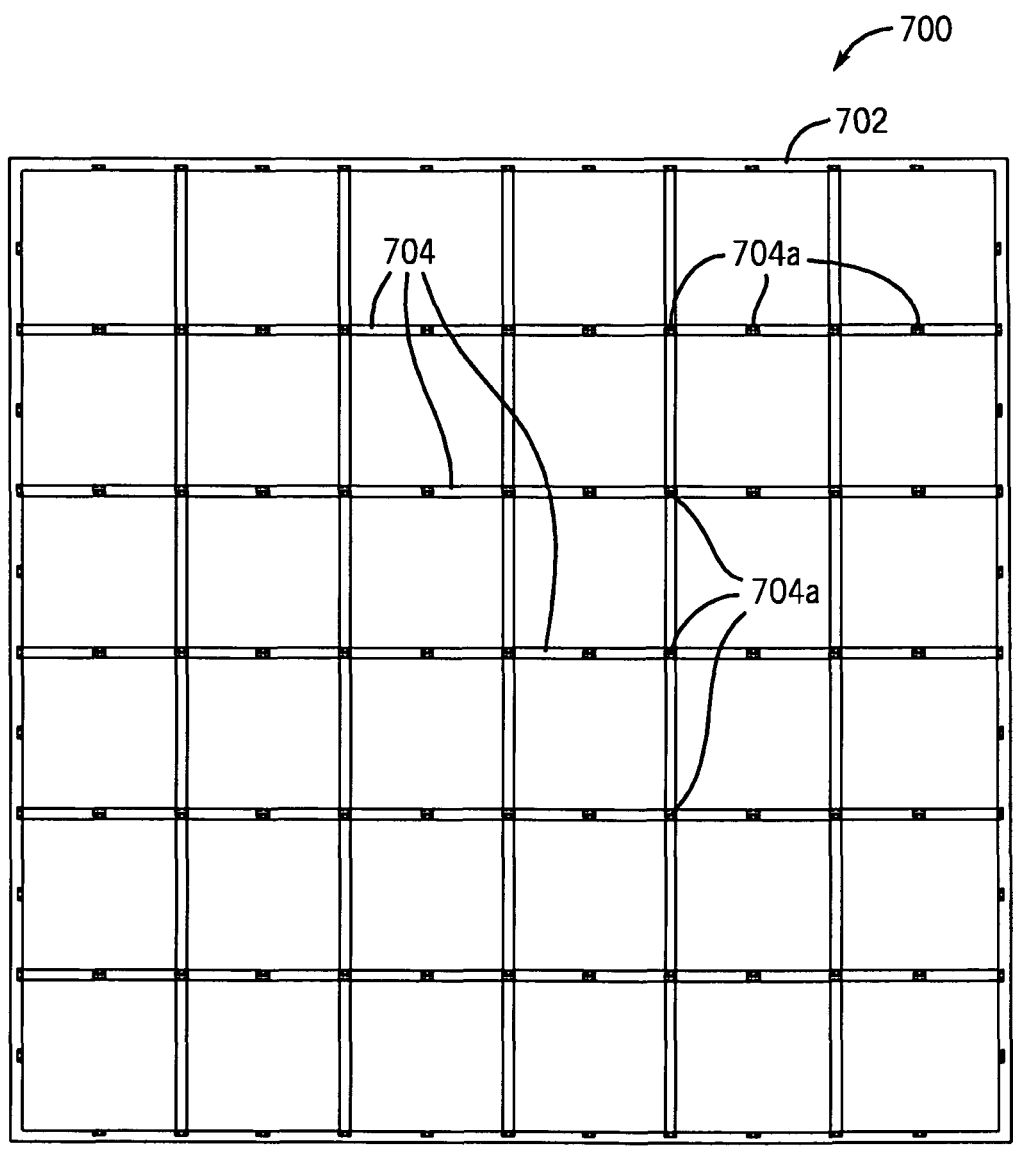
FIG. 6C is a top plan view of an antenna board suitable for use with the system for managing the inventory of reagents described herein. In this drawing, dividers have been laid over the antenna board in order to provide a 6×6 array configuration.

FIG. 6C is a top plan view of an antenna board 700 wherein a frame 702 and a set of elongated dividers 704 have been laid over the antenna board 700 in order to provide a 6×6 array configuration. The frame 702 has a plurality of slots 702a for receiving tabs (not shown) located at the ends of the elongated dividers 704. The elongated dividers 704 also have a plurality of slots 704a for allowing the elongated dividers 704 running from left to right to intersect with elongated dividers 704 running from front to rear and remain within the horizontal planes of the frame 702. It should be noted that the elongated dividers 704 running from left to right are identical with the elongated dividers 704 running from front to rear; however, the slots 704a in the elongated dividers 704 running from left to right face upwardly and the slots (not shown) in the elongated dividers 704 running from front to rear face downwardly so that the slots 704a in the elongated dividers 704 running from left to right interlock with the slots (not shown) in the elongated dividers 704 running from front to rear.

Figure 6D:
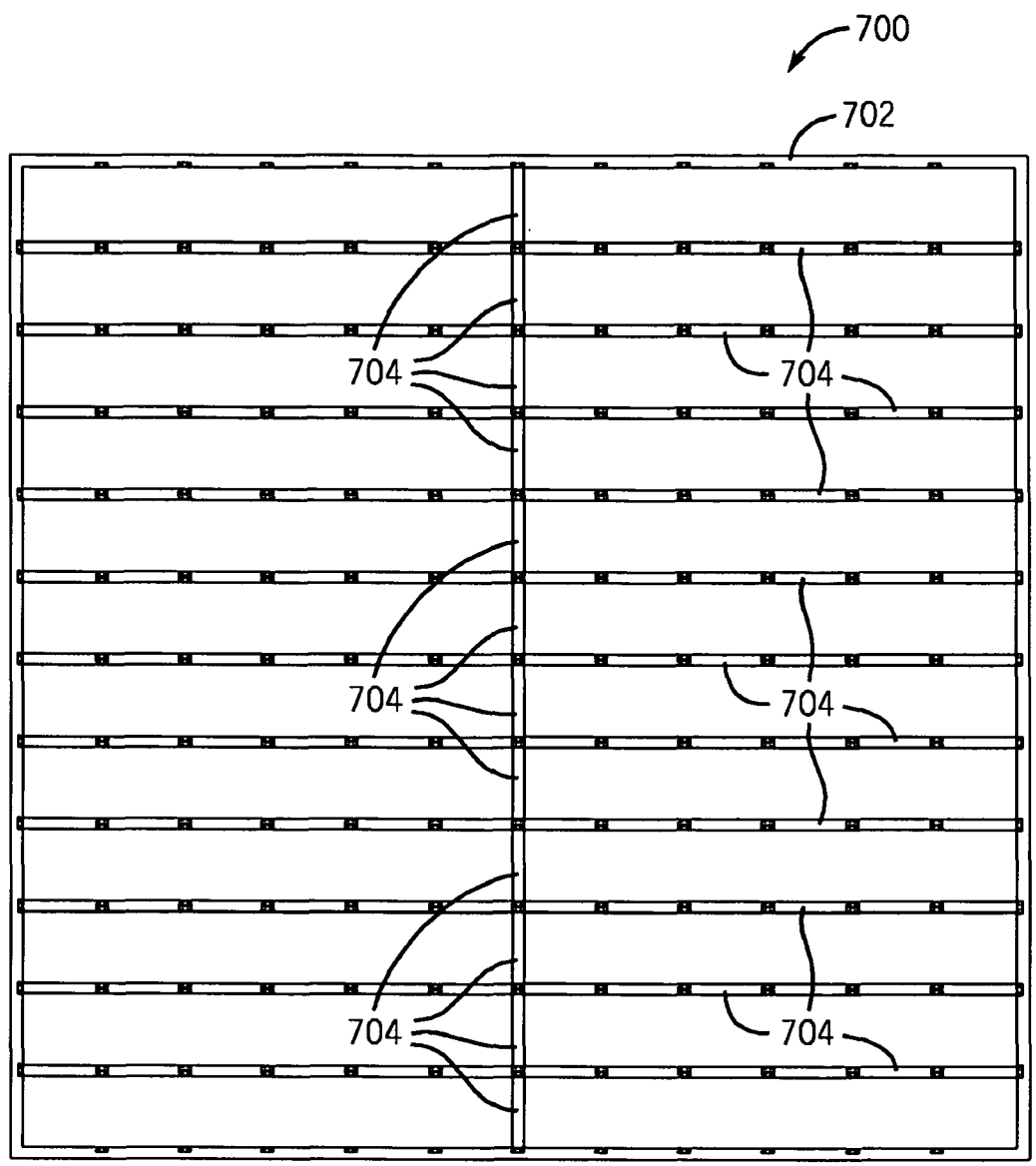
FIG. 6D is top plan view of an antenna board suitable for use with the system for managing the inventory of reagents described herein. In this drawing, dividers have been laid over the antenna board in order to provide a 2×12 array configuration.

FIG. 6D is a top plan view of an antenna board 700 wherein a frame 702 and a set of elongated dividers 704 have been laid over the antenna board 700 in order to provide a 2×12 array configuration. The frame 702 has a plurality of slots 702a for receiving tabs (not shown) located at the ends of the elongated dividers 704. The elongated dividers 704 also have a plurality of slots 704a for allowing the elongated dividers 704 running from left to right to intersect with the elongated divider 704 running from front to rear and remain within the horizontal planes of the frame 702. It should be noted that the elongated dividers 704 running from left to right are identical with the elongated dividers 704 running from front to rear; however, the slots 704a in the elongated dividers 704 running from left to right face upwardly and the slots (not shown) in the elongated dividers 704 running from front to rear face downwardly so that the slots 704a in the elongated dividers 704 running from left to right interlock with the slots (not shown) in the elongated dividers 704 running from front to rear.

Figure 6E:
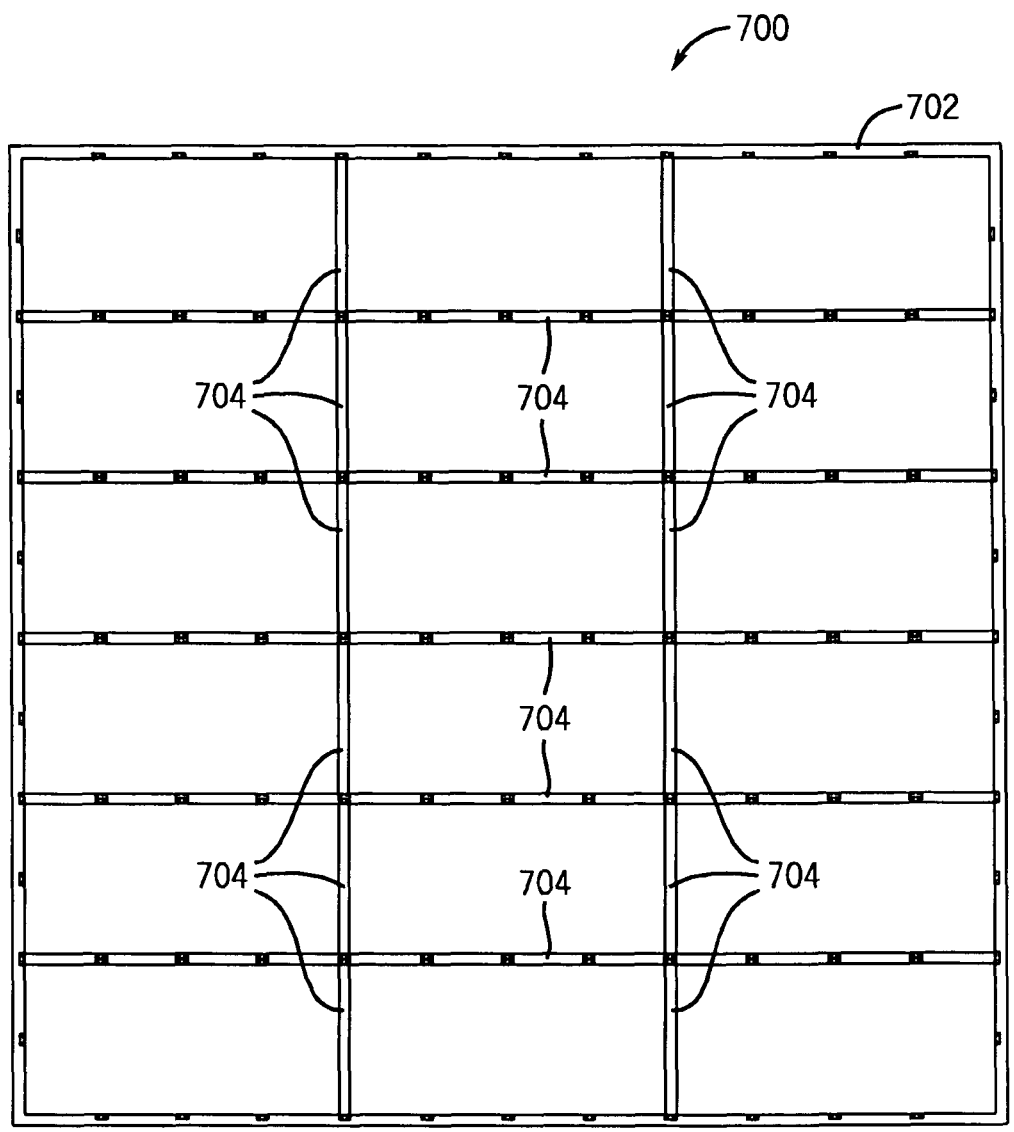
FIG. 6E is a top plan view of an antenna board suitable for use with the system for managing the inventory of reagents described herein. In this drawing, dividers have been laid over the antenna board in order to provide a 3×6 array configuration.

FIG. 6E is a top plan view of an antenna board 700 wherein a frame 702 and a set of elongated dividers 704 have been laid over the antenna board 700 in order to provide a 3×6 array configuration. The frame 702 has a plurality of slots 702a for receiving tabs (not shown) located at the ends of the elongated dividers 704. The elongated dividers 704 also have a plurality of slots 704a for allowing the elongated dividers 704 running from left to right to intersect with elongated dividers 704 running from front to rear and remain within the horizontal planes of the frame 702. It should be noted that the elongated dividers 704 running from left to right are identical with the elongated dividers 704 running from front to rear; however, the slots 704a in the elongated dividers 704 running from left to right face upwardly and the slots (not shown) in the elongated dividers 704 running from front to rear face downwardly so that the slots 704a in the elongated dividers 704 running from left to right interlock with the slots (not shown) in the elongated dividers 704 running from front to rear.

Figure 6F:
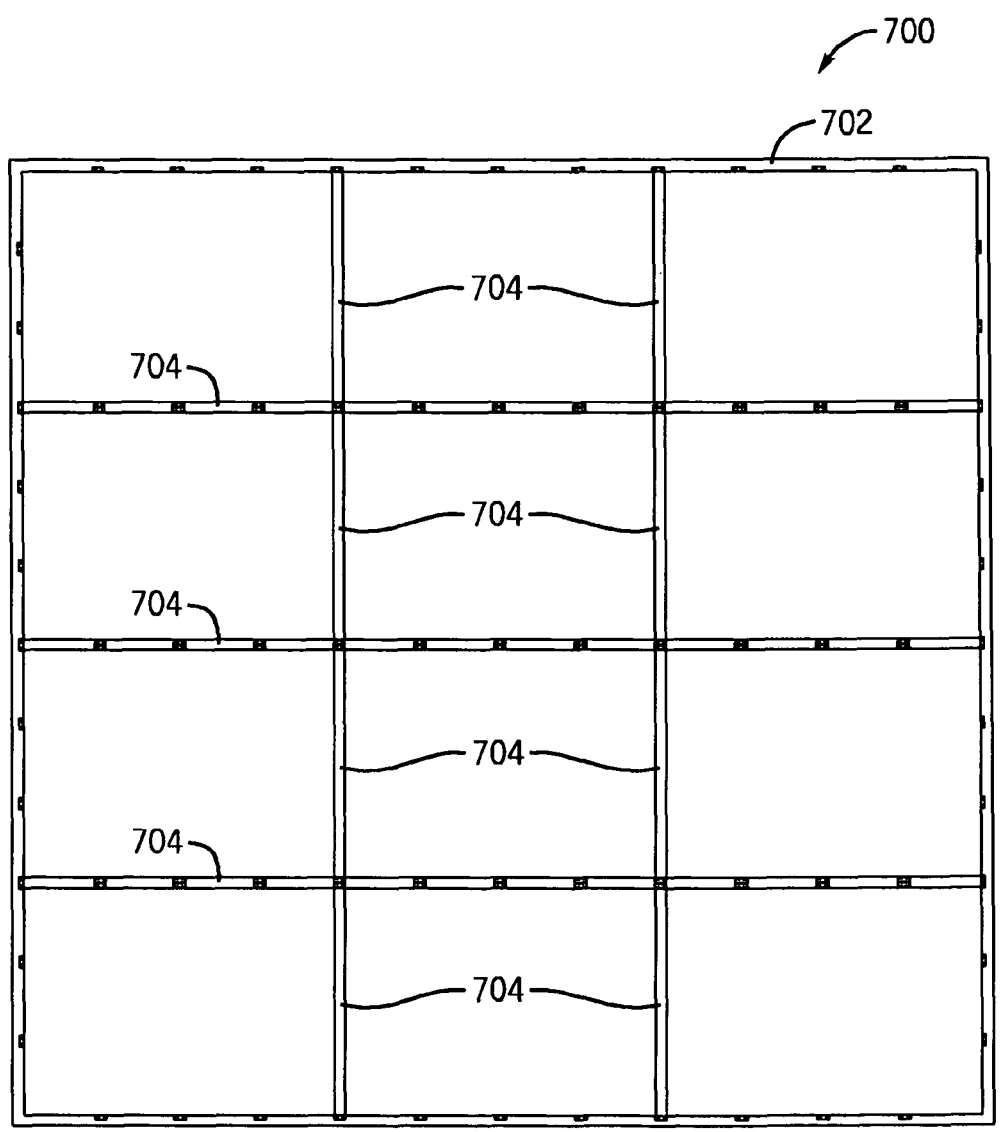
FIG. 6F is a top plan view of an antenna board suitable for use with the system for managing the inventory of reagents described herein. In this drawing, dividers have been laid over the antenna board in order to provide a 3×4 array configuration.

FIG. 6F is a top plan view of an antenna board 700 wherein a frame 702 and a set of elongated dividers 704 have been laid over the antenna board 700 in order to provide a 3×4 array configuration. The frame 702 has a plurality of slots 702a for receiving tabs (not shown) located at the ends of the elongated dividers 704. The elongated dividers 704 also have a plurality of slots 704a for allowing the elongated dividers 704 running from left to right to intersect with the elongated dividers 704 running from front to rear and remain within the horizontal planes of the frame 702. It should be noted that the elongated dividers 704 running from left to right are identical with the elongated dividers 704 running from front to rear; however, the slots 704a in the elongated dividers 704 running from left to right face upwardly and the slots (not shown) in the elongated dividers 704 running from front to rear face downwardly so that the slots 704a in the elongated dividers 704 running from left to right interlock with the slots (not shown) in the elongated dividers 704 running from front to rear.

Figure 6G:
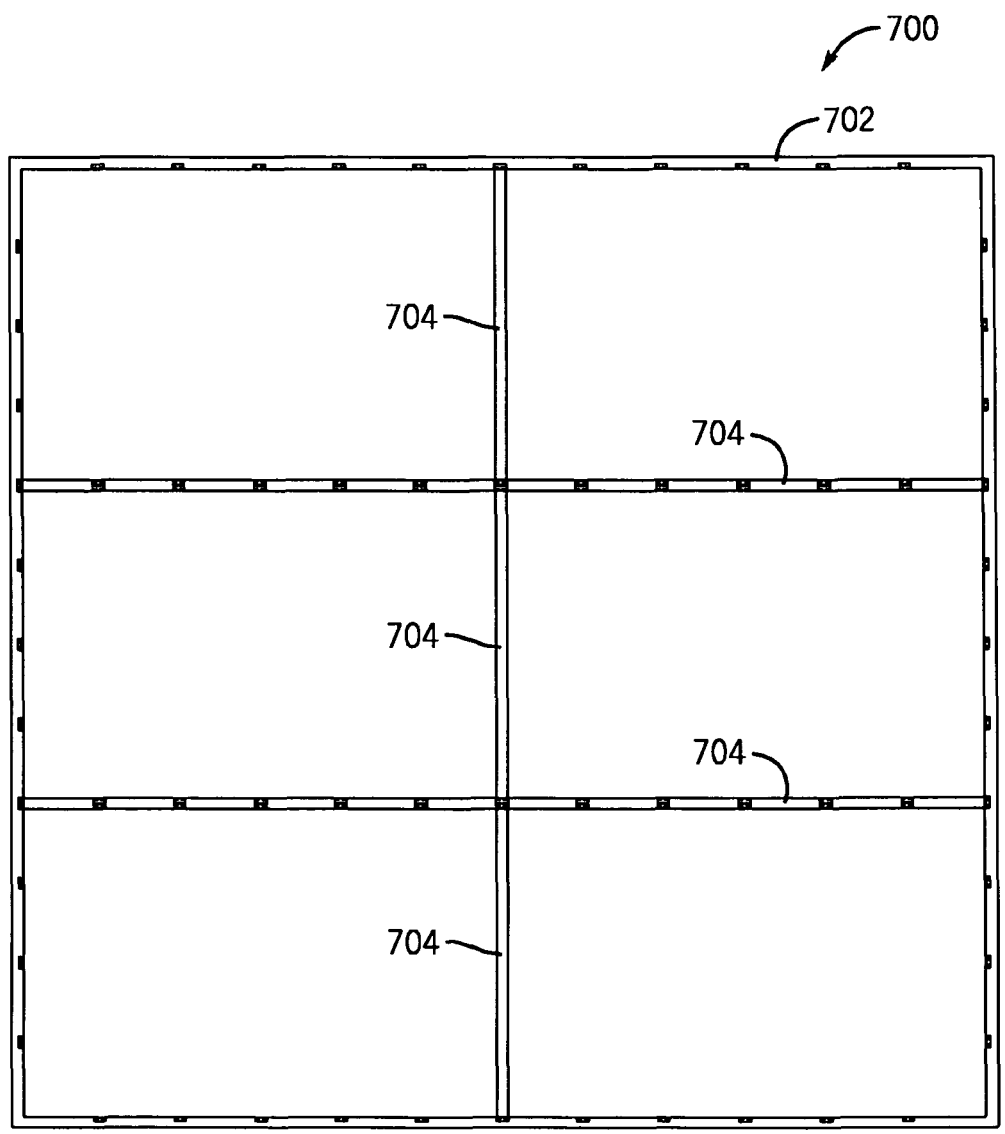
FIG. 6G is a top plan view of an antenna board suitable for use with the system for managing the inventory of reagents described herein. In this drawing, dividers have been laid over the antenna board in order to provide a 2×3 array configuration.

FIG. 6G is a top plan view of an antenna board 700 wherein a frame 702 and a set of elongated dividers 704 have been laid over the antenna board 700 in order to provide a 2×3 array configuration. The frame 702 has a plurality of slots 702a for receiving tabs (not shown) located at the ends of the elongated dividers 704. The elongated dividers 704 also have a plurality of slots 704a for allowing the elongated dividers 704 running from left to right to intersect with the elongated divider 704 running from front to rear and remain within the horizontal planes of the frame 702. It should be noted that the elongated dividers 704 running from left to right are identical with the elongated dividers 704 running from front to rear; however, the slots 704a in the elongated dividers 704 running from left to right face upwardly and the slots (not shown) in the elongated dividers 704 running from front to rear face downwardly so that the slots 704a in the elongated dividers 704 running from left to right interlock with the slots (not shown) in the elongated dividers 704 running from front to rear.

Figure 6H:
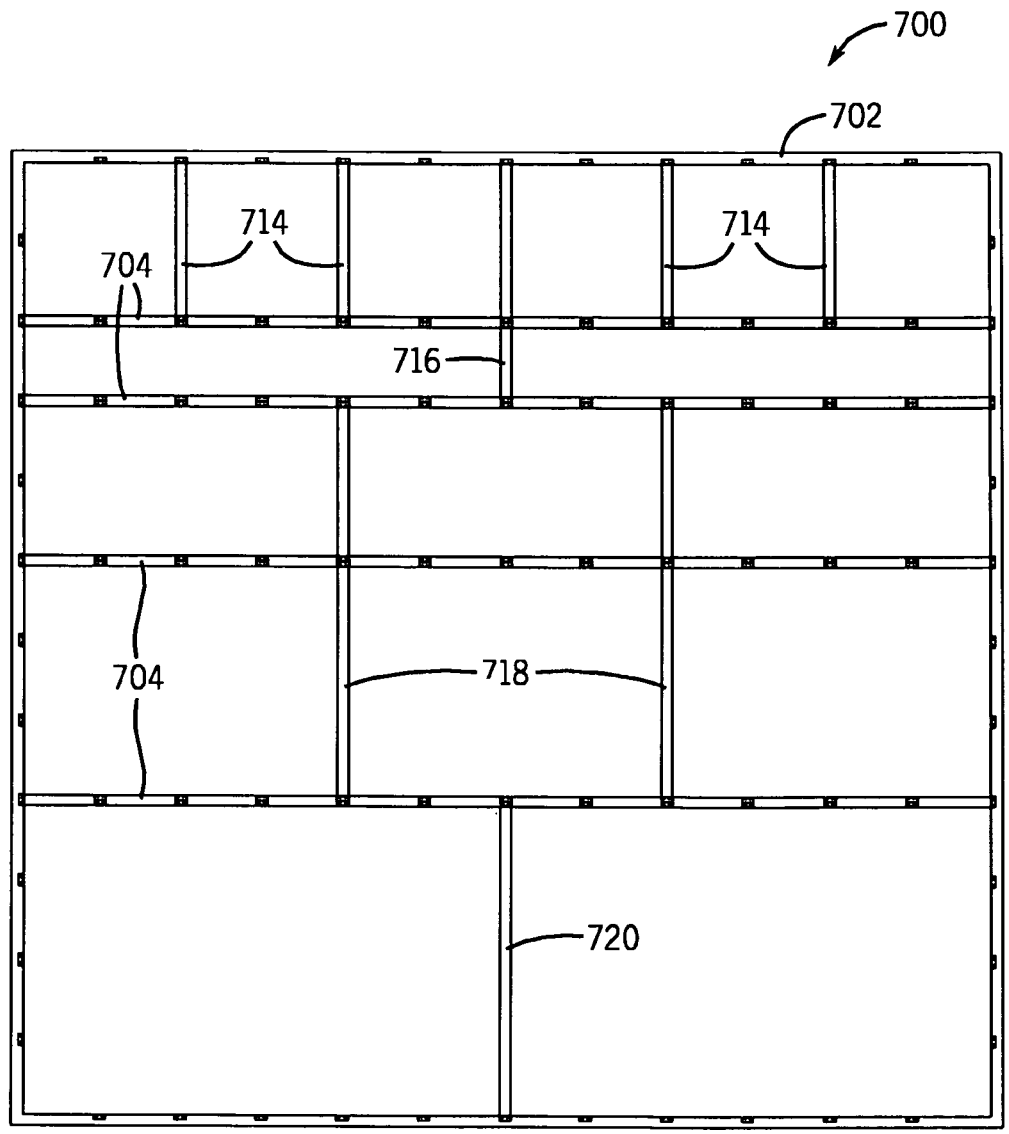
FIG. 6H is a top plan view of an antenna board suitable for use with the system for managing the inventory of reagents described herein. In this drawing, dividers have been laid over the antenna board in order to provide a custom array configuration.

FIG. 6H is a top plan view of an antenna board 700 wherein a frame 702 and a set of elongated dividers 704, 714, 716, 718, 720 have been laid over the antenna board 700 in order to provide a custom array configuration. The frame 702 has a plurality of slots 702a for receiving tabs (not shown) located at the ends of the elongated dividers 704, 714, 716. The elongated divider 704 also has a plurality of slots 704a for allowing the elongated dividers 718, 720 to intersect with elongated divider 704 or to receive the tabs (not shown) located at the ends of the elongated dividers 718, 720 and thereby allow the dividers 704, 714, 716, 718, 720 to remain within in the horizontal planes of the frame 702. It should be noted that the slots 704a in the elongated dividers 704 running from left to right face upwardly and the slots (not shown) in the elongated dividers 716, 718 running from front to rear face downwardly so that the slots 704a in the elongated dividers 704 running from left to right interlock with the slots (not shown) in the elongated dividers 716, 718 running from front to rear.

FIG. 7 shows the functional architecture (and sub-systems) of a system 800 for managing inventories of reagents. A real time controller 802 connected to the smart refrigerator interfaces with each of the following sub-systems:
  (a) track of the laboratory automation system 804;
  (b) radio frequency identification antenna selector 806;
  (c) radio frequency identification reader 808;
  (d) septum application robot 810;
  (e) de-capper robot 812;
  (f) pick and place robot 814;
  (g) cooling engine for the refrigerator 816;
  (h) local user interface 818;
  (i) system for managing inventories of reagents 820. The track of the laboratory automation system 804 routes reagents to specific clinical analyzers for placement into the inventory for the specific clinical analyzers. The radio frequency identification antenna selector 806 enables the real time controller 802 of the smart refrigerator to select any location for reading the radio frequency identification signals from a particular radio frequency identification tag at the selected location. The radio frequency identification reader 808 is a low power reader in compliance with ISO 14443 and ISO 15693 at 13.56 MHz. The septum application robot 810 installs a septum on an uncapped reagent container. The de-capper robot 812 removes caps from reagent containers and disposes of the removed caps. The pick and place robot 814 allows access to reagents and the input/output module. The pick and place robot 814 can also invert reagent containers to resuspend microparticles in the liquid phase of the reagent. The cooling engine for the refrigerator 816 enables the refrigeration of reagents at a temperature ranging from about 2° C. to about 8° C. The local user interface 818 is an interface provides a minimal amount of information, such as, for example, status, temperature, and the like, so that an operator does not have to refer to the main computer. The reagent inventory management component 820 communicates with the controller 802 of the smart refrigerator to account for and record the following types of information:
  (a) configuration information for the smart refrigerator
  (b) identification information for the smart refrigerator
  (c) calibration status of the smart refrigerator
  (d) built-in tests (BIT) of the smart refrigerator
  (e) inventory information for the smart refrigerator The software for management of inventories of reagents can be installed on a personal computer in the customer's facility. The software for managing of inventories of reagents can monitor inventory of reagents in the clinical analyzer(s) and send routing commands to the smart refrigerator(s) to replenish the reagents consumed by clinical analyzer(s). The software for managing of inventories of reagents can monitor the inventory of reagents in the smart refrigerator(s) and send orders to the supplier's ordering system to replenish consumable items. These orders are sent without intervention or can be reviewed and modified by the customer. The software for managing of inventories of reagents can prioritize the reagents routed from the smart refrigerator(s) to the clinical analyzer(s) by serving the analyzer most in need of replenishment of reagents, utilizing calibrated reagents, utilizing oldest reagents, utilizing opened reagents, distributing menu to maximize throughput and/or workflow. The software for managing of inventories of reagents can manage reagent recalls, shipping and storage temperature records, as well as assay protocols, material safety data, package inserts, and assay calibration.

In order to maximize the number of customers using the system for managing inventory of reagents, several configuration options have been defined to allow tailoring of each system installation to best meet the needs of a customer.

The components of the system for managing of inventories of reagents include at least one clinical analyzer, a controller for managing of inventories of reagents, and a smart refrigerator. The architecture of the smart refrigerator can be simplified to allow manual loading and unloading of reagent kits and customer open storage (both refrigerated and frozen). The system for managing of inventories of reagents can perform all the software functions previously described. However, containers to be removed manually can be identified and placed in an analyzer (with a computer display and/or other visual indicators). The smart refrigerator can merely provide temperature control and radio frequency identification interrogating capability.

A standard system for managing of inventories of reagents can include the components of the system for managing of inventories of reagents described above along with features to enable loading special reagent carriers that allow manual transport of reagents to be loaded in an analyzer. The system for managing of inventories of reagents can perform all the software functions previously described, but can identify reagent carriers to be manually transported to an analyzer (with a computer display and/or other visual indicators). The smart refrigerator can provide all of the functions previously described, except the laboratory automation system interface to the analyzers. These functions can include controlling temperature, reading radio frequency identification tags, agitating containers containing suspensions containing microparticles prior to placing the containers on a clinical analyzer, removing caps from containers, installing septa on containers, etc.

The fully automated system for managing of inventories of reagents can include the standard features plus features to enable automated transport of reagents to be loaded or unloaded from clinical analyzer(s). Other than initial loading of reagent kits, no intervention by the operator is required.

A central reagent storage area (not shown) can provide a substantial inventory of reagents; these reagents can be transported to a track system or to an analysis section of the laboratory automation system, as required. Means of transportation suitable for transporting reagents from the central storage area to a track system or to an analysis section of the laboratory automation system include, but are not limited to, gantries, endless conveyor belts, and robotic mechanisms.

A plurality of antennas, which are traces on a printed circuit board, function as separate stationary radio frequency identification readers. These antennas can receive separate collections of data. In a preferred embodiment of a reader for reading radio frequency identification tags, a single printed circuit board has a plurality of antennas under the reagent storage area and the sample storage area. The antennas can read radio frequency identification tags attached to reagent containers, preferably to the bottoms of reagent containers. As indicated previously, antenna boards are described in U.S. patent application Ser. No. 11/495,430, filed Jul. 28, 2006, and entitled SYSTEM FOR TRACKING VESSELS IN AUTOMATED LABORATORY ANALYZERS BY RADIO FREQUENCY IDENTIFICATION and U.S. patent application Ser. No. 12/274,479, filed Nov. 20, 2008, and entitled SYSTEM FOR TRACKING VESSELS IN AUTOMATED LABORATORY ANALYZERS BY RADIO FREQUENCY IDENTIFICATION, both of which have previously been incorporated herein by reference.

The system for managing inventory of reagents can employ a radio frequency identification system to identify objects. A printed circuit board for the radio frequency identification system can provide connections for remote antennas and a means for selecting those antennas one at a time. For example, the radio frequency identification system can have external connections for several remote reading locations, such as the micro-well plate rotator, pre-treatment area, magnetic particle processor, luminescence reader(s), absorbance reader(s), inventory reading locations, and locations on the local queue and transport track. By reading the antennas at these remote locations, a micro-well plate can be tracked throughout the laboratory automation system and provide a chain of custody.

In order to implement the radio frequency identification system described herein, a radio frequency identification tag can be positioned on the lowermost portion of a container, e.g., a reagent container 30. It is often desirable to position an encapsulated radio frequency identification tag on the lowermost portion of a container.

Writable radio frequency identification tags can be used to update radio frequency identification tags to reflect changes that have taken place with respect to the contents of the containers equipped with the radio frequency identification tags. The radio frequency identification system can provide an interface to personal computer. As discussed previously, the reagent containers 30 can be equipped with radio frequency identification tags, which can be read by an automated radio frequency identification reader (not shown) positioned below the sub-section 62 of the analysis section 60. A radio frequency identification reader can read and update radio frequency identification tags on reagent containers 30 and on sample containers 18 (or on sample container carriers 24) when aspirating of a portion of the reagent or a portion of the sample is carried out or an operation for scanning the items in inventory is initiated. Information of the type shown in TABLE I can be updated on the radio frequency identification tags by the radio frequency identification reader.

Radio frequency identification tags can be permanently applied to a given component, i.e., container, either by means of a molding process or by means of a bonding process. Radio frequency identification tags applied by molding or bonding are not re-usable. However, radio frequency identification tags can be rendered re-usable by ensuring that reagent containers, sample containers, or micro-well plates are destroyed and the radio frequency identification tags recovered.

Reading radio frequency identification tags and writing radio frequency identification tags can be performed using ISO protocols 14443, 15693, or 18000, all of which are incorporated herein by reference, or combinations of the foregoing ISO protocols. These protocols utilize a three-layer communication model:

(a) application layer
(b) communication layer
(c) physical layer. The three-layer communication model, primarily the communication layer, will provide the functions of error detection, error correction, identity authentication, collision avoidance, etc. These functions can be considered automatic, because they are part of the protocol for enabling the radio frequency identification reader to communicate with the radio frequency identification tag.

The application layer handles the information contained in the radio frequency identification tag. Such information can include at least some of the information in TABLE I:

TABLE I

| Class of data | Specific data |
|---|---|
| Tag identifier | Unique identifier for container |
| Manufacturing data | (a) Revision number(s) of reagent(s) |
| | (b) Serial number(s) of reagent(s) |
| | (d) Component identifier(s) |
| | (e) Lot number(s) of reagent(s) |
| | (f) Stability/expiration data for reagent(s) |
| | (g) Times/dates of manufacture of reagent(s) |
| | (h) Configuration(s) of assay(s) |
| | (e.g., number of reagent containers needed) |
| | (i) Number of tests in container(s) |
| | (j) Associated components of assay(s) |
| | (k) Calibration data for assay(s) |
| | (l) Material safety data sheet |
| | (m) Assay protocol |
| | (n) Package insert |
| Shipping and storage data | (a) Temperature(s) of reagent during shipping |
| | (b) Times/dates of shipping movements and storage periods |
| | (c) Locations and dates of storage periods |
| Analyzer and usage data | (a) Times/dates of opening(s) of reagent container(s) |
| | (b) Number of aspirations from reagent container(s) |
| | (c) Carryover and potential contamination or dilution of reagent(s) or sample(s) |
| | (d) Encryption algorithms for protection of data |
| | (e) Other algorithms to ensure integrity of data |
| | (f) Tracking chain of custody of reagent container(s) and sample container(s) |

An area located in front of an analysis section (see, for example, item 60 in FIG. 1), can be used as a radio frequency identification read zone for micro-well plates. A system for utilizing radio frequency identification tags and radio frequency identification readers is described in U.S. patent application Ser. No. 11/495,430, filed Jul. 28, 2006, and entitled SYSTEM FOR TRACKING VESSELS IN AUTOMATED LABORATORY ANALYZERS BY RADIO FREQUENCY IDENTIFICATION and U.S. patent application Ser. No. 12/274,479, filed Nov. 20, 2008, and entitled SYSTEM FOR TRACKING VESSELS IN AUTOMATED LABORATORY ANALYZERS BY RADIO FREQUENCY IDENTIFICATION, both of which have previously been incorporated herein by reference.

In the system described herein, bulk reagents in liquid form can be employed. The use of bulk reagents in liquid form enables aspirating/dispensing devices having a plurality of pipettes to aspirate and dispense reagents at a high rate of throughput. Bulk liquids, such as, for example, a pre-trigger solution for certain types of immunoassays, wash buffer, and deionized water, are preferably contained in troughs (see, for example, items 116a, 116b, 116c, etc., in FIG. 1), so that a plurality of pipette tips 110 can aspirate a specific liquid simultaneously. Other bulk liquids can be stored where appropriate. For example, the trigger solution for certain types of immunoassays, which is used in conjunction with the pre-trigger solution, can be stored in a reader, such as, for example, a luminescence reader, whereby the trigger solution is released at the point when the results of the assay are to be read. The trigger solution enables photons to be emitted from the label of the reaction product of the immunoassay within from about 3 to about 5 seconds.

The architecture provides for refrigerated storage of the reagents on the shelves of the smart refrigerator, uploading of storage and shipping temperature records (via radio frequency identification tag on reach package), microparticle agitation prior to placement on the analyzer, cap removal, septum installation, automated loading of reagent carriers (manually transported to analyzers), automated transport of reagents to clinical analyzers (via a track of a laboratory automation system), refrigerated storage of controls and calibrators, refrigerated storage of bulk liquids (such a trigger and pre-trigger solutions), unloading of reagent carriers, unloading of reagents from clinical analyzers, user definable refrigerated storage, and user definable freezer storage.

Manual loading of reagents and samples can be eliminated by using automated systems. In addition, ordering of reagents and other consumable items can be automated by means of a system for managing inventories of reagents, which can communicate with on-line order entry systems available from many vendors. The system for managing the inventory of reagents described herein provides substantial labor savings and quality improvements relative to manual management of inventory of reagents and consumable items.

The system for managing the inventory of reagents described herein can manage inventories of reagents and consumable items with data that can be encoded on a radio frequency identification tag. For example, if a partially used reagent container is moved to a new system, that system can determine how many assays remain in the container, when the container was opened, and temperature tracking data for reagent shipping and storage, by reading the data that is stored on a radio frequency identification tag.

Expiration dates, calibration status, and reagent inventory needs of clinical analyzers can be monitored to provide automated reagent loading and ordering. These features allow laboratories to save labor that is typically allocated to these functions.

The system described herein can facilitate the monitoring of supply contracts. The system described herein can facilitate forecasting by suppliers and help to improve factory utilization of suppliers. The system facilitates in reducing waste caused by expiration of reagents and suboptimum usage of sizes of containers. In addition, data on package inserts can be consolidated into an electronic format, thereby reducing excessive waste of paper. Still further, the system provides meaningful guidance for changes in material.

Operation

The reagent containers 30 can be loaded by the operator into a smart refrigerator when the reagent containers 30 are received in a shipping carton from a shipping department. This loading process may require removing the top of the shipping carton. The radio frequency identification tags (not shown) affixed to the reagent containers 30 can be read by a radio frequency identification reader (not shown) associated with the smart refrigerator and the inventory is recorded. When an analysis section 60 of the laboratory automation system 10 connected to the system for managing the inventory of reagents requests a reagent container(s) 30, the system for managing the inventory of reagents typically removes the oldest calibrated reagent(s) of the type requested from a shipping carton in the smart refrigerator, i.e., in a first-in, first-out manner, prepares the reagent container(s) 30 for processing (e.g., caps are removed, septa are installed, etc.) and places the reagent container(s) 30 into reagent container carrier(s). Removal of the reagent container 30 from the shipping carton and placement of the reagent container 30 into the reagent container carrier can be carried out by means of a robotic mechanism (not shown). The reagent container carriers holding the reagent containers 30 are then diverted onto the appropriate lane of the track system 12 and subsequently routed to the analysis section 60 of the laboratory automation system 10 that requested the reagent(s). Eventually, empty shipping cartons are ejected from the smart refrigerator into a solid waste container. The items shown in FIG. 1 are described in greater detail in U.S. patent application Ser. No. 12/257,495, filed Oct. 24, 2008, and entitled AUTOMATED ANALYZER FOR CLINICAL LABORATORY, previously incorporated herein by reference.

Various modifications and alterations of this disclosure will become apparent to those skilled in the art without departing from the scope and spirit of this disclosure, and it should be understood that this disclosure is not to be unduly limited to the illustrative embodiments set forth herein.

What is claimed is:

1. A method comprising:
   automatically determining a first inventory of a plurality of consumable items in a plurality of refrigerators;
   automatically determining a second inventory of the plurality of consumable items in a plurality of clinical analyzers;
   automatically managing the movement of at least one of the consumable items from at least one of the refrigerators to at least one the clinical analyzers based on the first inventory and the second inventory.

2. The method of claim 1, wherein managing the movement comprises:
   providing a refrigerator assignment;
   providing a clinical analyzer assignment; and
   providing a route.

3. The method of claim 1, wherein the consumable item comprises a reagent.

4. The method of claim 1 further comprising prioritizing the use of the consumable items.

5. The method of claim 4, wherein the prioritizing is based on the ages of the consumable items.

6. The method of claim 4, wherein the prioritizing is based on a recall status of the consumable items.

7. The method of claim 4, wherein the prioritizing is based on a calibration of the consumable items.

8. The method of claim 4, wherein the prioritizing is based on a use level of the consumable items.

9. The method of claim 1 further comprising:
   determining a recall status of a consumable item; and
   quarantining a recalled consumable item.

10. The method of claim 1, wherein the consumable items comprise radio frequency identification tags to identify the consumable items.

11. The method of claim 1, wherein the refrigerators include one or more shelves comprising an antenna to detect the presence or absence of at least one of the consumable items.

12. The method of claim 1, wherein the refrigerators comprise reconfigurable shelving to accommodate packaging of consumable items in multiple sizes.

13. The method of claim 12, wherein the shelving comprises a plurality of releasably interlocking and reconfigurable dividers.

14. The method of claim 1 further comprising automatically monitoring and updating supply contracts for the consumable items.

\* \* \* \* \*